United States Patent
Melvin et al.

(10) Patent No.: US 8,790,308 B2
(45) Date of Patent: Jul. 29, 2014

(54) ADAPTABLE OBTURATOR FOR VARIOUS SIZED TROCARS

(71) Applicant: Applied Medical Resources Corporation, Rancho Santa Margarita, CA (US)

(72) Inventors: Christina N. Melvin, Rancho Santa Margarita, CA (US); Melissa C. Melendrez, Rancho Santa Margarita, CA (US); Kareem Elsayed, Rancho Santa Margarita, CA (US); Babak Jasemian, Rancho Santa Margarita, CA (US); Matthew M. Becerra, Rancho Santa Margarita, CA (US); Jeremy J. Albrecht, Rancho Santa Margarita, CA (US); Gary M. Johnson, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 13/752,045

(22) Filed: Jan. 28, 2013

(65) Prior Publication Data

US 2013/0197439 A1 Aug. 1, 2013

Related U.S. Application Data

(60) Provisional application No. 61/592,931, filed on Jan. 31, 2012.

(51) Int. Cl.
*A61M 5/178* (2006.01)

(52) U.S. Cl.
USPC ............ 604/164.01; 604/167.01; 604/170.01; 604/170.02

(58) Field of Classification Search
USPC .................. 604/117, 164.01–164.02, 167.01, 604/170.01–170.02
See application file for complete search history.

(56) References Cited

U.S. PATENT DOCUMENTS

| | | | |
|---|---|---|---|
| 958,854 A | | 5/1910 | Bunn |
| 2,907,321 A | * | 10/1959 | Rubens .................. 600/104 |
| 4,712,536 A | | 12/1987 | Hawks |
| 5,144,942 A | | 9/1992 | Decarie et al. |
| 5,222,487 A | | 6/1993 | Carr et al. |

(Continued)

FOREIGN PATENT DOCUMENTS

| | | |
|---|---|---|
| WO | WO 01/26559 | 4/2001 |
| WO | WO 2010/045253 | 4/2010 |
| WO | WO 2012/044959 | 4/2012 |

OTHER PUBLICATIONS

European Patent Office, International Search Report and the Written Opinion for international application No. PCT/US2013/023458, title "Adaptable Obturator for Various Sized Trocars", mailed Mar. 19, 2013.

(Continued)

*Primary Examiner* — Theodore Stigell
(74) *Attorney, Agent, or Firm* — Patrick Y. Ikehara

(57) ABSTRACT

Surgical access systems and obturators for or used in surgical access systems are provided. The obturator is configured to operate or accommodate the use of at least two different sized trocars. The outer diameter of the adaptable obturator when inserted into a trocar compresses from an initial condition to a compressed condition to match the inner diameter of the trocar.

17 Claims, 26 Drawing Sheets

(56) References Cited

U.S. PATENT DOCUMENTS

| | | |
|---|---|---|
| 5,284,474 A | 2/1994 | Adair |
| 5,546,937 A | 8/1996 | Stuart et al. |
| D385,628 S | 10/1997 | Echevarria |
| 5,824,002 A | 10/1998 | Gentelia et al. |
| 5,843,039 A | 12/1998 | Klemm |
| 6,007,544 A | 12/1999 | Kim |
| D449,104 S | 10/2001 | Baker et al. |
| D449,887 S | 10/2001 | Haberland et al. |
| 6,558,353 B2 | 5/2003 | Zohmann |
| 6,755,794 B2 | 6/2004 | Soukup |
| 7,473,221 B2 | 1/2009 | Ewers et al. |
| 7,686,823 B2 | 3/2010 | Pingleton et al. |
| 7,758,603 B2 * | 7/2010 | Taylor et al. ............ 606/185 |
| 7,931,623 B2 | 4/2011 | Wing et al. |
| 2004/0199165 A1 | 10/2004 | Culbert et al. |
| 2005/0209627 A1 | 9/2005 | Kick et al. |
| 2007/0051375 A1 | 3/2007 | Milliman |
| 2007/0239108 A1 | 10/2007 | Albrecht et al. |
| 2007/0270752 A1 | 11/2007 | Labombard |
| 2009/0030375 A1 | 1/2009 | Franer et al. |
| 2009/0182282 A1 | 7/2009 | Okihisa et al. |
| 2009/0187079 A1 | 7/2009 | Albrecht et al. |
| 2009/0281500 A1 | 11/2009 | Acosta et al. |
| 2009/0306586 A1 | 12/2009 | Ross et al. |
| 2010/0094227 A1 | 4/2010 | Albrecht et al. |
| 2010/0280368 A1 | 11/2010 | Can et al. |
| 2010/0324488 A1 | 12/2010 | Smith |
| 2012/0095297 A1 | 4/2012 | Dang et al. |

OTHER PUBLICATIONS

GelPoint® Advanced Access Platform Spec Sheet, Applied Medical Resources, Oct. 2010, 2 pages.
International Searching Authority—EPO, International Search Report and Written Opinion of the International Searching Authority for International Application No. PCT/US2011/054266, mailed Feb. 9, 2012, 11 pages.

\* cited by examiner

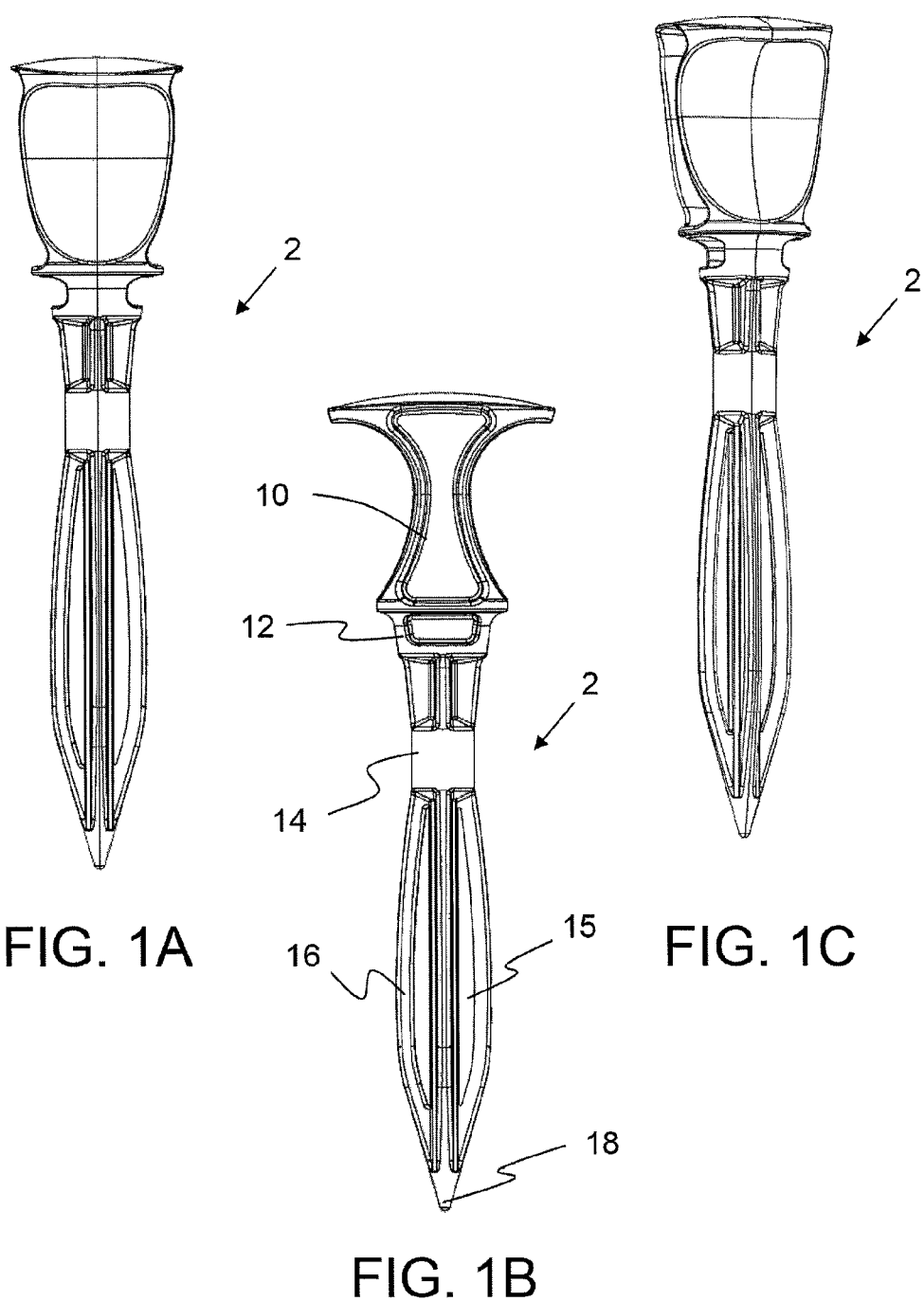

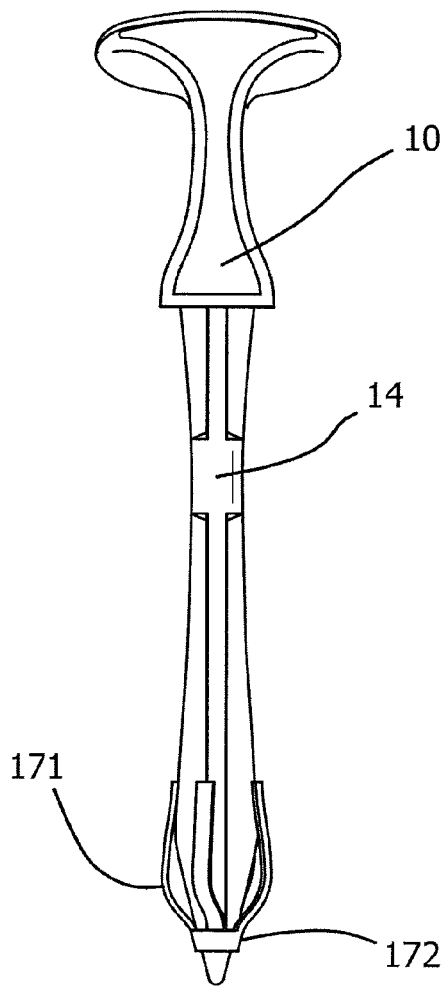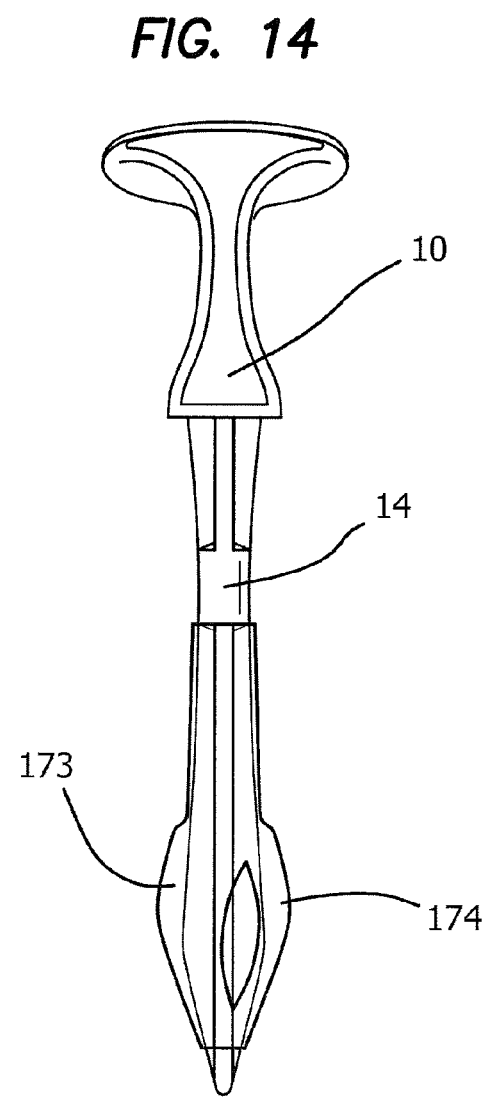
FIG. 13
FIG. 14

FIG. 15-6
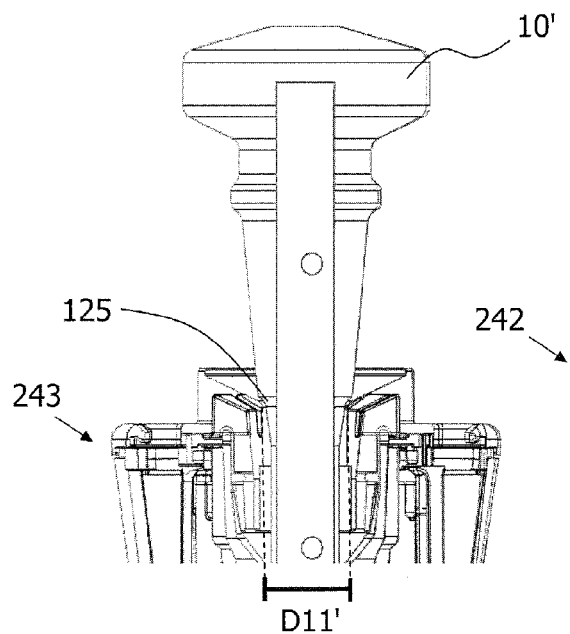
FIG. 15-7
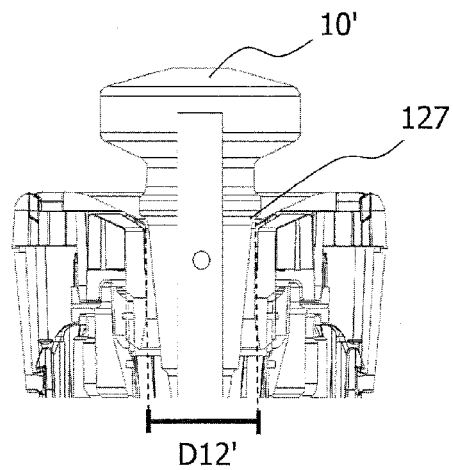
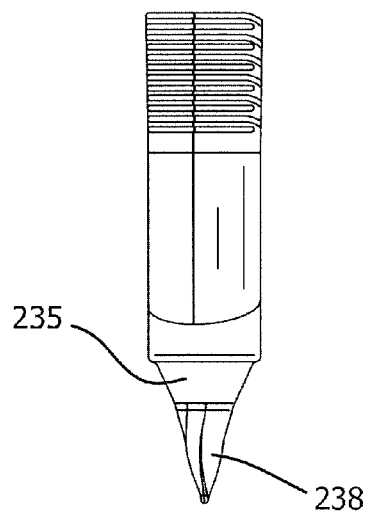
FIG. 15-8
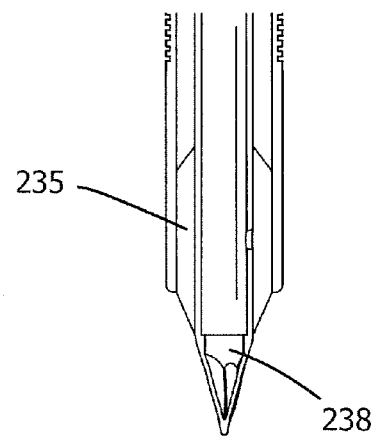
FIG. 15-9

US 8,790,308 B2

ADAPTABLE OBTURATOR FOR VARIOUS SIZED TROCARS

CROSS-REFERENCE TO RELATED APPLICATIONS

This application claims the benefit 61/592,931, filed on Jan. 31, 2012, the entire disclosure of which is hereby incorporated by reference as if set forth in full herein.

BACKGROUND

This application relates generally to surgical access systems and, more specifically, to obturators for or used in surgical access systems.

Surgical access systems facilitate minimally invasive surgery across a body wall and within a body cavity. For example, in abdominal surgery, trocars alone or in conjunction with other access devices provide a working channel across the abdominal wall to facilitate the use of instruments within the abdominal cavity. Trocar systems can include a cannula, which provides the working channel, and an obturator that is used to place the cannula across a body wall, such as the abdominal wall. The obturator is inserted into the working channel of the cannula and pushed through the body wall with a penetration or insertion force of sufficient magnitude to result in penetration of or entry through the body wall. Once the cannula has traversed the body wall, the obturator can be removed.

With the cannula in place, various instruments may be inserted through the cannula into the body cavity. One or more cannulas may be used during a procedure. These cannulas or trocars may be of different sizes, e.g., different diameters and lengths, to accommodate different sized or dimensioned instruments. Using an arrangement of trocars versus using the largest sized trocar is often more desirable to minimize trocar site defects and the invasiveness of the surgical procedure. Additionally, the largest sized trocars often do not accommodate small sized instruments as for example the instrument seals of such trocars are not sufficient to prevent the escape of gas when such small sized instruments are used. During the procedure, the surgeon manipulates the instruments in the cannulas, sometimes using more than one instrument at a time. A reduction in insertion force of a trocar into the body cavity is desired to prevent, reduce or eliminate uncontrolled entry into the body cavity and potential damage to organs, tissue or other prior inserted devices in the cavity and the incision or surgical access site.

SUMMARY

Generally, an obturator is provided to operate or accommodate the use of at least two different trocars. In one embodiment, an obturator is configured to be insertable into a trocar cannula. The obturator may include an elongate shaft having a proximal end and a distal end, a handle at the proximal end of the elongate shaft, a tip at the distal end of the elongate shaft, and a compressible portion at the tip of the shaft, the compressible portion provided to operate and accommodate the use of at least two different sized trocars.

In one embodiment, a trocar system is provided. The system comprises a first trocar having a seal assembly and a cannula with a diameter and a length and a second trocar having a seal assembly and a cannula with a diameter larger than the diameter of the first trocar and a length greater than the length of the first trocar. The system comprises an adjustable obturator having a compressible portion in an initial state configured to have a diameter greater or equal to the diameter of the second trocar and in a compressed state configured to have a diameter greater or equal to the diameter of the first trocar and having a diameter smaller than the diameter of the second trocar.

These and other features of the invention will become more apparent with a discussion of embodiments in reference to the associated drawings.

BRIEF DESCRIPTION OF THE DRAWINGS

The present inventions may be understood by reference to the following description, taken in connection with the accompanying drawings in which the reference numerals designate like parts throughout the figures thereof.

FIG. 1A is a side view of an obturator in accordance with various embodiments of the present invention.

FIG. 1B is a side view of an obturator in accordance with various embodiments of the present invention.

FIG. 1C is a side view of an obturator in accordance with various embodiments of the present invention.

FIG. 15-2 is a bottom view of an obturator in accordance with various embodiments of the present invention.

FIG. 15-3 is a perspective view of an obturator in accordance with various embodiments of the present invention.

FIG. 15-4 is a side view of an obturator in accordance with various embodiments of the present invention.

FIG. 15-5 is a side view of a compressed obturator in accordance with various embodiments of the present invention.

FIG. 15-6 is a cross-sectional view of an obturator and an exemplary small trocar in accordance with various embodiments of the present invention.

FIG. 15-7 is a cross-sectional view of an obturator and an exemplary large trocar in accordance with various embodiments of the present invention.

FIG. 15-8 is a side view of an obturator and an exemplary large trocar in accordance with various embodiments of the present invention.

FIG. 15-9 is a cross-sectional view of an obturator and an exemplary large trocar in accordance with various embodiments of the present invention.

FIG. 15-10 is a perspective view of an obturator and an exemplary large trocar in accordance with various embodiments of the present invention.

FIG. 15-11 is a bottom view of an obturator and an exemplary large trocar in accordance with various embodiments of the present invention.

FIG. 15-12 is a perspective view of an obturator and an exemplary small trocar in accordance with various embodiments of the present invention.

FIG. 15-13 is a bottom view of an obturator and an exemplary small trocar in accordance with various embodiments of the present invention.

FIG. 15-14 is a cross-sectional view of an obturator and an exemplary small trocar in accordance with various embodiments of the present invention.

FIG. 15-15 is a side view of an obturator and an exemplary small trocar in accordance with various embodiments of the present invention.

DETAILED DESCRIPTION

Figure 1D:
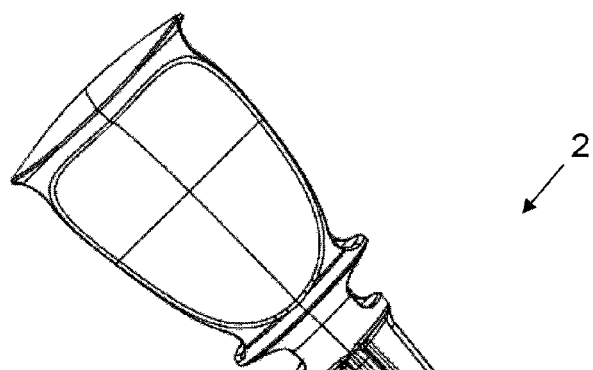
FIG. 1D is a perspective view of an obturator in accordance with various embodiments of the present invention.
Figure 1E:
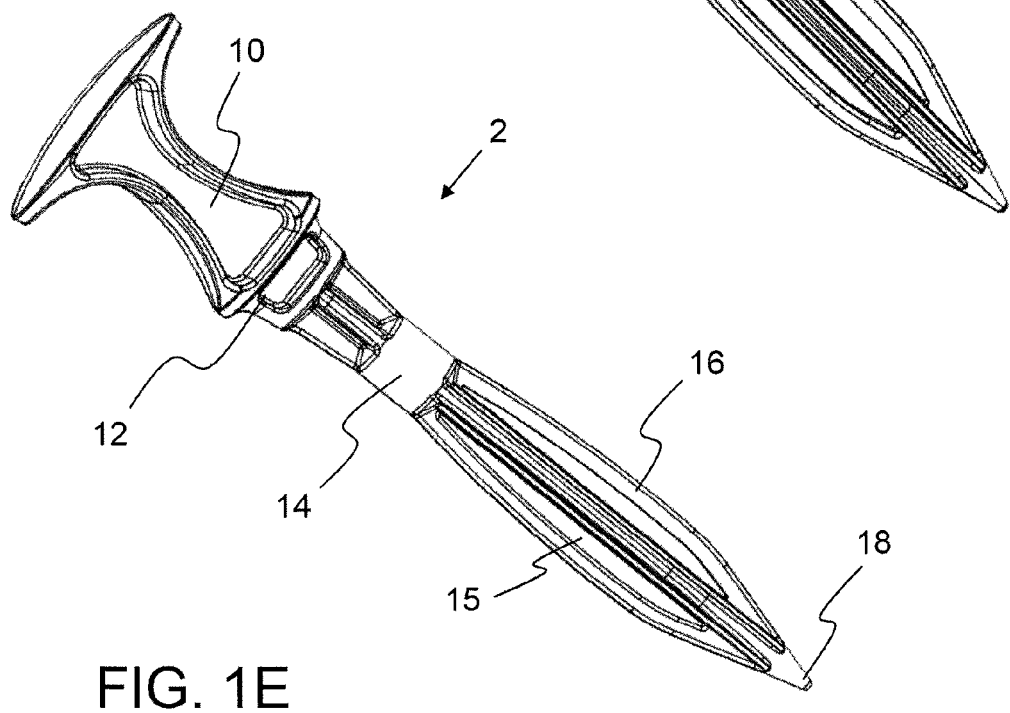
FIG. 1E is a perspective view of an obturator in accordance with various embodiments of the present invention.

An obturator is provided to operate or accommodate the use of at least two different trocars. For example, a first trocar, e.g., a 5-10 mm trocar, and a second trocar, e.g., a 5-12 mm trocar, are provided and differ in that the first trocar has an inner diameter that is smaller than the inner diameter of the second trocar to accommodate smaller diameter surgical instruments inserted therethrough. The first trocar is also shorter than the second trocar.

The obturator is compressible such that it can adjust to the different sizes posed by the at least two different trocars. For example, the outer diameter of the obturator when fully expanded or in its initial condition matches or mates with the inner diameter of the second "larger" trocar. The outer diameter of the obturator when inserted into the first trocar compresses from this initial condition to a compressed condition to match the inner diameter of the first trocar. The matching of the diameter of the obturator and the trocar or cannula removes tip wobble or general movement of the obturator and/or tip as the trocar is being inserted and thus facilitates insertion and placement of the trocar. Gaps or spacing within the shaft and/or compressible and/or elastic material incorporated into or coupled to the shaft of the obturator facilitates the compressibility of the obturator.

The single adjustable or adaptable obturator thereby replaces the need to provide at least two different sized obturators to accommodate the at least two different sized trocars and thus obviates the potential problem of using the wrong obturator with a particular trocar thereby avoiding for example operating room confusion. Additionally, savings in manufacturing, distribution and operational costs are realized. For example, packaging space that would be used for multiple obturators can be reduced to provide a single obturator and the cost savings in providing a single obturator instead of multiple obturators can also be significant.

Referring now to the figures, FIGS. 1A-1E provides various views of an obturator in accordance with various embodiments of the present invention. The obturator includes a handle 10 at the proximal portion or end of the obturator. The handle is graspable by a user, e.g., a surgeon, to insert and withdraw the obturator from a trocar and provides a base or support for a user to push the obturator against the trocar. The obturator includes a tip 18 at the distal end of the obturator and as illustrated is blunt and pointed. In various embodiments, the tip is rounded, sharp or otherwise dimensioned and shaped as desired or warranted by the surgical procedure or operational conditions of the use of the trocar and/or obturator.

Between the tip 18 and the handle 10 of the obturator is a core seal 14. The core seal 14 seals against the aperture of an instrument seal of a trocar. The core seal as illustrated is cylindrical and seals against one or more instrument seals of one or more different sized trocars, e.g., first or second trocars. As such, the diameter and length of the core seal is sufficient to effectuate such a seal.

Near the handle or proximal portion of the obturator, the obturator has an abutment or depth limiter 12 such that the most distal portion of the depth limiter will contact the cap of the first trocar to prevent further insertion of the obturator. A second or more proximal portion of the depth limiter is larger in diameter than the distal portion of the depth limiter and contacts the cap of the second trocar to prevent further insertion of the obturator. As such, whether a first or second trocar is used, the same amount of the tip portion of the obturator, e.g., portion L1 (FIG. 3), extends out the distal end of either trocar and thereby the same tip geometry relative to the trocars remains the same. By keeping both tip geometries the same or nearly the same, the insertion force needed to insert the obturator and trocar into the surgical site or access device remains the same or substantially similar and thus the same or substantially similar tactile feedback is maintained upon or during insertion of either different trocar using the same obturator. In one embodiment, the differences are shown at the proximal end of the obturator where a portion of the obturator extends further out from the proximal end of the trocar when the obturator is used with the smaller of the at least two trocars. The core seal 14 however ensures that the proximal end differences does not effect the seal between the obturator and the instrument seal which may become noticeable when the obturator and trocar are inserted into a surgical site or device under insufflation gas pressure.

The obturator also includes an adjustable, compressible and/or expandable portion and in various embodiments takes the form of ribs 16. The ribs 16 are spaced circumferentially around a center shaft of the obturator and separated from the center shaft by gaps 15. As shown, the ribs 16 extend from the core seal 14 to the tip 18. Four equally spaced ribs around the center shaft or longitudinal axis of the obturator are provided with obturator 2. Fewer or more ribs may be provided but are arranged such that the diameter defined by the one or more ribs to mate with the inner diameters of the various trocars to be used with the single obturator. The mating or conforming of the ribs 16 with the various sized trocars ensures that the obturator remains snug or closely fitted into the different sized trocars and thereby removing potential wobble or movement of the obturator within the trocar as the obturator and trocar are being inserted into the surgical site or through another access device.

In one embodiment, the ribs 16 in an initial or relaxed state are fully expanded and thus define or delimit a specific diameter. The specific diameter in one embodiment is equal to or is larger than the inner diameter of the largest sized trocar to be used with the obturator. The ribs 16 are compressible or can otherwise assume a flattened or non-expanded form or state and thus define or delimit another smaller diameter. This smaller diameter is equal to or greater than the inner diameter of the smallest sized trocar to be used with the obturator. The ribs 16 in one embodiment can assume a state or condition between the non-expanded and expanded form to define diameters between the smallest and largest sizes and thus can conform to the various inner diameter sizes of various different sized trocars between the smallest sized trocar to the largest sized trocar. The ribs 16 also being adjustable allows for changes within the inner diameter of the trocar that can vary within the trocar. For example, the inner diameter could be larger at the proximal end versus the diameter near the distal end or vary throughout the length of the trocar. The adjustability of the ribs thereby prevents the obturator from being snagged or otherwise blocked due to variances in the inner diameter throughout the trocar.

In one embodiment, the gap or space 15 between the rib and the center shaft of the obturator defines the compressibility or expandability of the obturator and thereby delimits the diameter and/or circumference defined. The mating of the ribs with the inner diameter of the trocar along with the core seal also limits potential movement or wobble due to proximal end differences of the trocar when inserted into different sized trocars.

Figure 2:
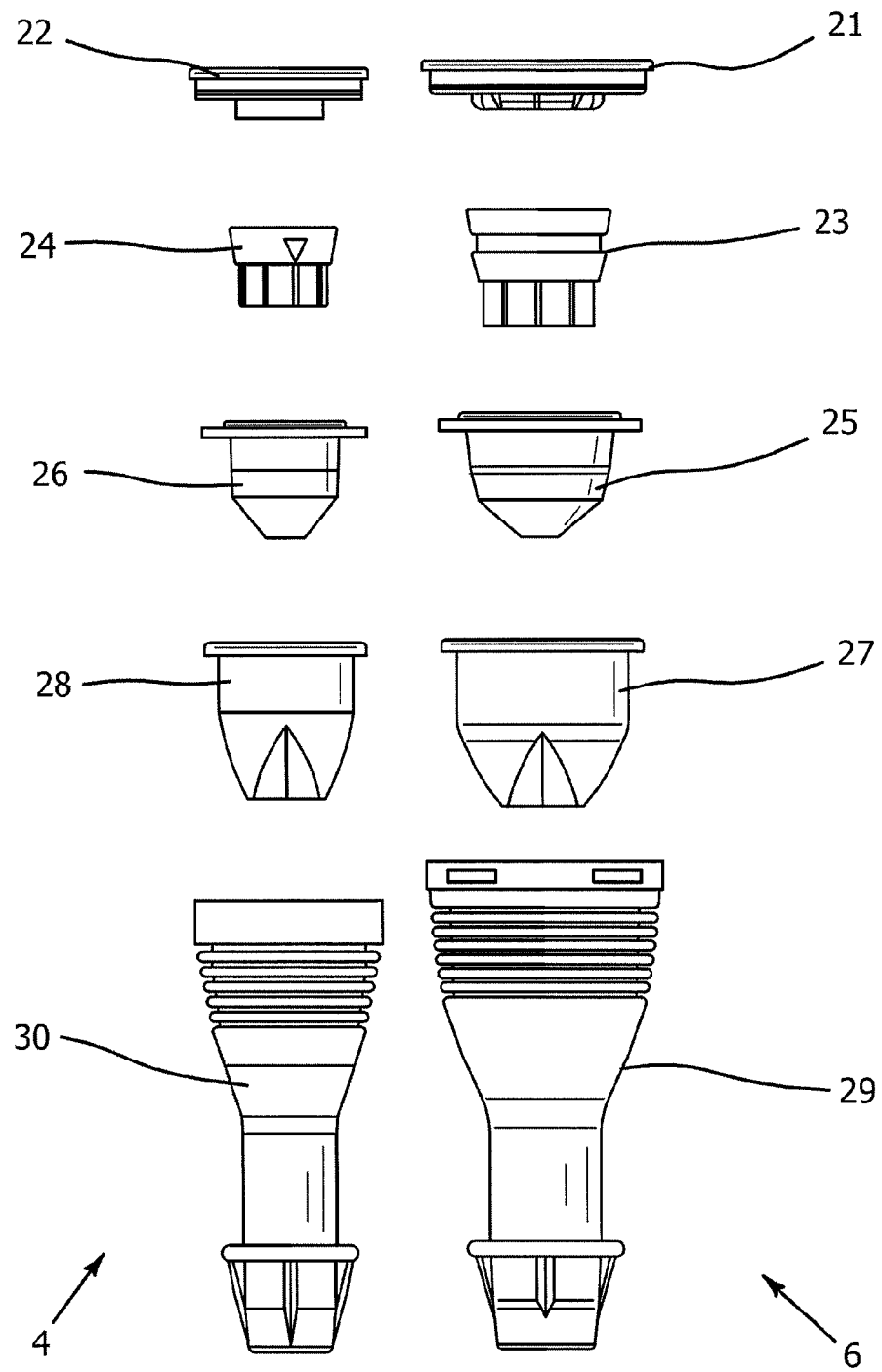
FIG. 2 illustrates exploded views of two exemplary trocars in accordance with various embodiments of the present invention.

In FIG. 2, two exemplary trocars are shown. It should be appreciated that multiple other trocars could be described with various other differences in size, shape and with more or less components provided in FIG. 2. Thus, the trocars provided should be viewed as non-limiting examples of trocars that can be accommodated by the various embodiments of the obturators described herein. As shown, trocar 4 is smaller than trocar 6 and thus is smaller in length and accommodates a smaller diameter or range of small instrument diameters versus the larger trocar 6. Each trocar includes a cap 21, 22; a seal protector 23, 24; an instrument or septum seal 25, 26; and zero seals 27, 28. The protectors and seals are disposed between a cap 21, 22 and trocar housing 29, 30. The instrument or septum seal seals the working channel of the trocar when an instrument is in place, and a zero closure valve or zero seal seals the working channel when the instrument is removed or in the absence of an instrument.

It should be appreciated that the trocar as described throughout may include a seal or valve housing coupled or attached to a cannula with the valve housing holding the instrument seal and/or zero seal. The cannula is affixed or removably connected to the valve housing. The cannula in one embodiment may hold the zero seal or portions of the instrument and/or zero seal may extend into a portion of the cannula. Also, the housing and cannula could be combined or formed into a single incorporated or monolithic structure thereby making where the housing ends and the cannula begins indistinguishable. The instrument and zero seals in various embodiments may also be combined or formed as a single seal. The cannula may include ribs, threads, projections or retainers along or at the distal end of the cannula to hold or retain the cannula within the surgical site and/or an access device. In various embodiments, the trocar is a monolithic structure with seals provided within a proximal portion of the trocar. Also, in various embodiments, the trocar is rigid and not bendable.

As illustrated, the overall trocar length of the first trocar is smaller than the overall trocar length of the second trocar and for exemplary purposes for parts of the description the first trocar represents the smallest trocar to be used with the obturator and the second trocar represents the largest trocar to be used with the obturator. The inner diameter of the first trocar is also smaller than the inner diameter of the second trocar. The overall length of the obturator as provided in various embodiments is larger than the first and second trocars with proximal and distal portions of the obturator extending beyond the respective proximal and distal ends of the trocars with the obturator inserted therethrough.

Figure 3:
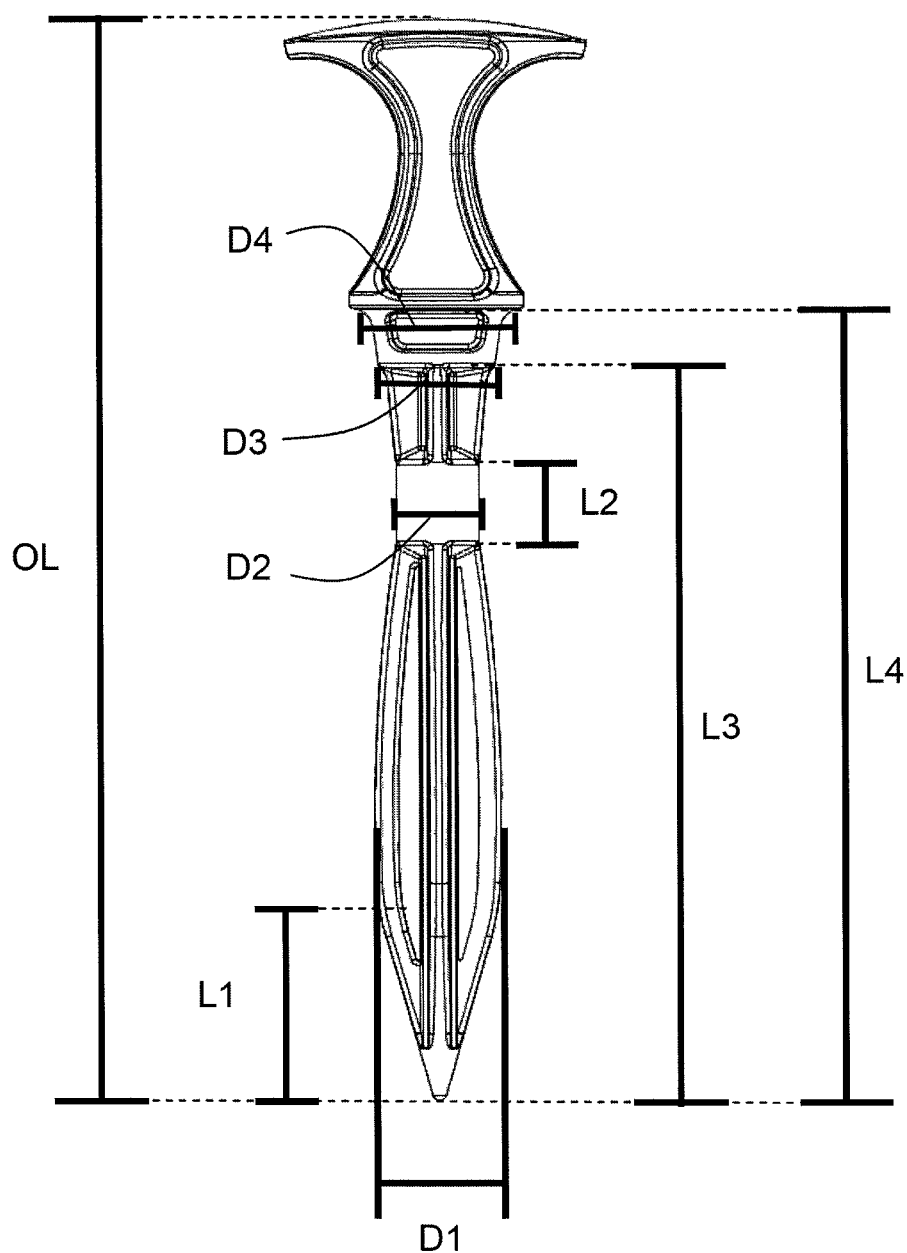
FIG. 3 is a side view of an obturator in accordance with various embodiments of the present invention.
Figure 4:
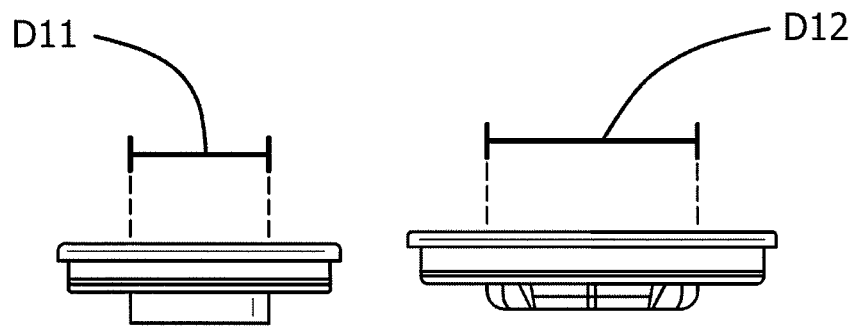
FIG. 4 illustrates side views of the proximal portions of the exemplary trocars in accordance with various embodiments of the present invention.
Figure 5:
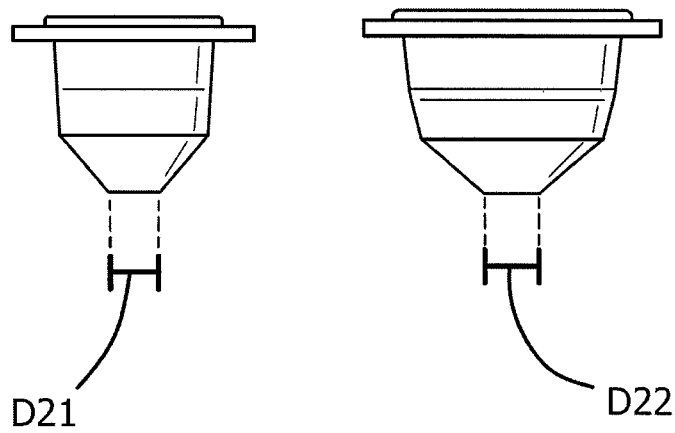
FIG. 5 illustrates side views of the instrument seals of the exemplary trocars in accordance with various embodiments of the present invention.

Referring now also to FIGS. 3-5, in one embodiment, the obturator in an initial or expanded (partially or fully) state defines a diameter and/or width D1 that is equal to or greater than the inner diameter of the largest cannula to be used with the obturator. As such, in one state or condition the obturator defines or delimits a diameter and/or width D1 that is equal to or greater than the inner diameter of the largest cannula to be used with the obturator. Additionally, in a separate state or condition, the obturator defines or delimits a diameter and/or width that is equal to or greater than the inner diameter of the smallest cannula to be used with the obturator. This second defined diameter is smaller than the diameter D1. The obturator in various embodiments may have various other states or conditions between these two states or conditions in which the obturator defines or delimits a diameter and/or width that smaller than the inner diameter of the largest cannula to be used with the obturator (or diameter D1) and larger than the inner diameter of the smallest cannula to be used with the obturator.

The overall length OL of the obturator remains constant. The stepped portion or depth limiter 12 in one embodiment defines or includes one or more expanded portions. For example, a first expanded portion is positioned a first length L3 measured starting from the tip or distal most portion of the obturator to a position on the obturator past the core seal 14. The first length L3 is smaller than the overall length OL. A second expanded portion is positioned a second length L4 measured from the tip or distal most portion of the obturator to a position on the obturator past the core seal 14.

In various embodiments, the first and/or second expanded portions are positioned ahead of or adjacent to the handle portion 10 of the obturator 2. In one embodiment, the first and/or second expanded portions are blended into or formed as part of the handle portion 10 of the obturator 2. As such, the handle portion 10 defines a first and/or second expanded portion. In one embodiment the depth limiter is tapered or graduated having or defining a first distal diameter and graduating, tapering or having steps to one or more larger sections, portions, flanges or abutments having or defining one or more larger proximal diameters.

The first expanded portion abuts against the cap or proximal portion of the valve housing or trocar of the smallest cannula to be used with the obturator when the obturator is inserted into the trocar. However, the first expanded portion does not abut against the cap or proximal portion of the valve housing or trocar of the largest trocar or a larger trocar than the smallest trocar when the obturator is inserted into this trocar. In one embodiment, the first expanded portion moves pass the cap or proximal portion of the largest trocar and a second expanded portion abuts against the cap or proximal portion of the trocar of the largest trocar.

The first expanded portion of obturator 2 as illustrated defines a first diameter D3 that is smaller than the diameter D4 defined by the second expanded portion. The first diameter D3 equals or is larger than the diameter of D11 of the proximal portion or cap of trocar 4 and trocar 4 for exemplary purposes represents the smallest trocar to be used with the obturator. As such, when the obturator is inserted into the trocar, the first expanded portion contacts the cap or outer surface of the cap of the trocar to prevent further distal or insertion of the obturator into the trocar. The first diameter D3 is however smaller than the diameter of D12 of the proximal portion or cap of trocar 6 and trocar 6 for exemplary purposes represents the largest trocar to be used with the obturator or at least larger than the first trocar. When the obturator is inserted into trocar 6, the first expanded portion does not contact the cap or outer surface of the trocar and thus travels further into the trocar 6. The second expanded portion of the obturator as illustrated defines a second diameter D4. The second diameter D4 is greater than the first diameter D3 and the diameter D11 of the trocar 4. The second diameter D4 equals or is larger than the diameter of D12 of the proximal portion or cap of trocar 6. Thus, when the obturator continues to be inserted into the trocar 6, the second expanded portion contacts the cap or outer surface of the cap to prevent further distal movement or insertion of the obturator into the trocar 6. Accordingly, the obturator is allowed to or is not restricted from advancing farther into a trocar with a larger inner diameter than a trocar with a smaller inner diameter.

In one embodiment, the portion of the obturator extending out from the distal end of the smallest cannula with the obturator fully inserted there through and the portion of the obturator extending out from the distal end of the largest cannula with the obturator fully inserted there through are the same. As such, the same tip geometry (e.g., shape, dimensions, length, width and/or diameter) is provided by the obturator even though different length trocars or cannulas are used. For example, in the illustrated embodiment, the distal length L1 of the obturator 2 that would extend out from the distal end of trocars 4 and 6, for example, remains the same even with the overall lengths of the trocars being different. The tip of the obturator in one embodiment with the obturator fully inserted within various sized trocars has or defines an outer surface or circumference that is flushed with the distal end of the trocar. As provided in the illustrated embodiment, the length of trocar 4 is smaller than the length of the trocar 6 with both trocar lengths being smaller than the overall length of the obturator 2.

The length L2 of the core seal 14 in one embodiment is equal or larger than the difference in length L3 and L4 as defined by the respective first and second expanded portions of the obturator. As such, the length of the core seal ensures that the outer surface of the obturator abuts against the aperture of the instrument seals of the various sized trocars to ensure that a seal is maintained between the obturator and the instrument seal. The position of the core seal along the obturator can vary and depends on the size, placement and/or dimensions of the instrument seal and/or the aperture or opening of the instrument seal of the various trocars. In various embodiments, the length of the core seal can also be increased to account for such variations in the instrument seals of the various trocars. The size or dimensions of the core seal can vary to reduce the amount of material utilized to form the core seal, to increase/decrease the size or dimensions of the depth limiter and/or the compressible portion to increase/decrease compressibility and/or to accommodate different trocar lengths, housing sizes or shapes and/or to avoid restricting or interfering with the depth limiter and/or the compressible portion.

The diameter D2 of the core seal 14 is equal or greater than the diameter D21 and D22 of the apertures through the instrument seals 25, 26. As such, the core seal with the obturator inserted into the trocar maintains a seal against the aperture of the various sized instrument seals of the various sized trocars to be used with the obturator.

Figure 6:
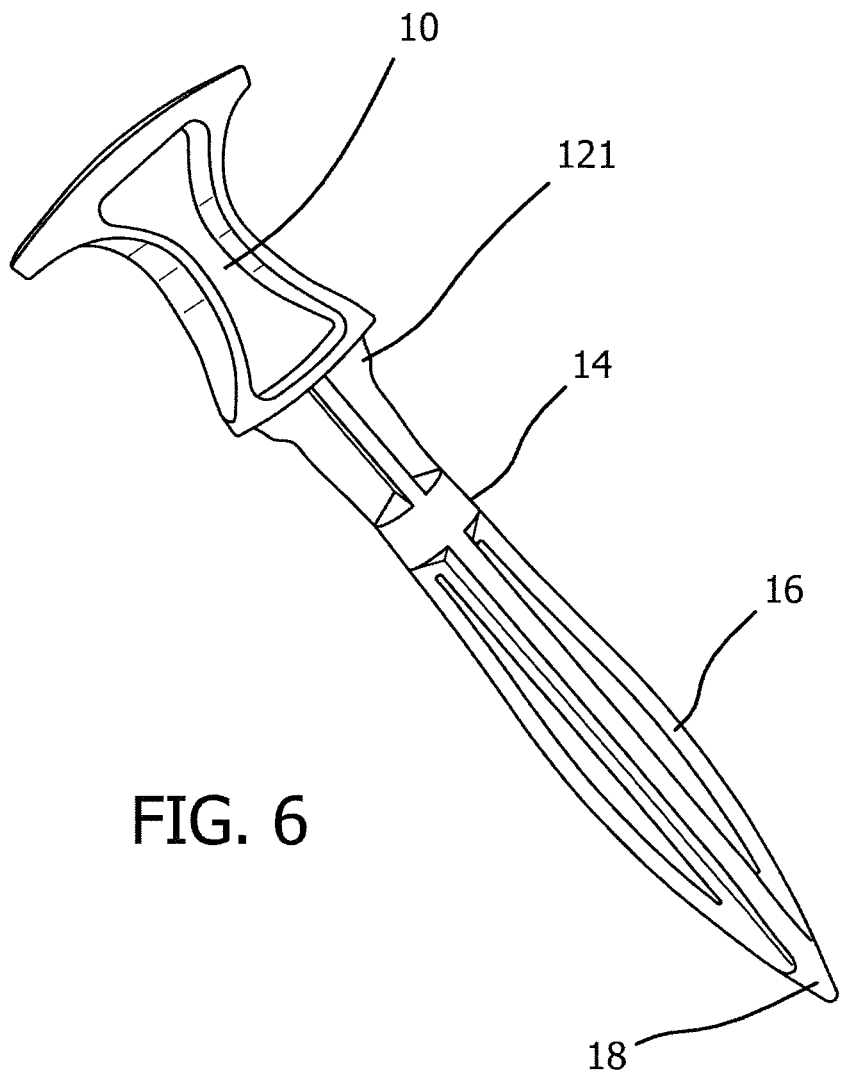
FIG. 6 is a perspective view of another embodiment of an obturator in accordance with various embodiments of the present invention.
Figure 7:
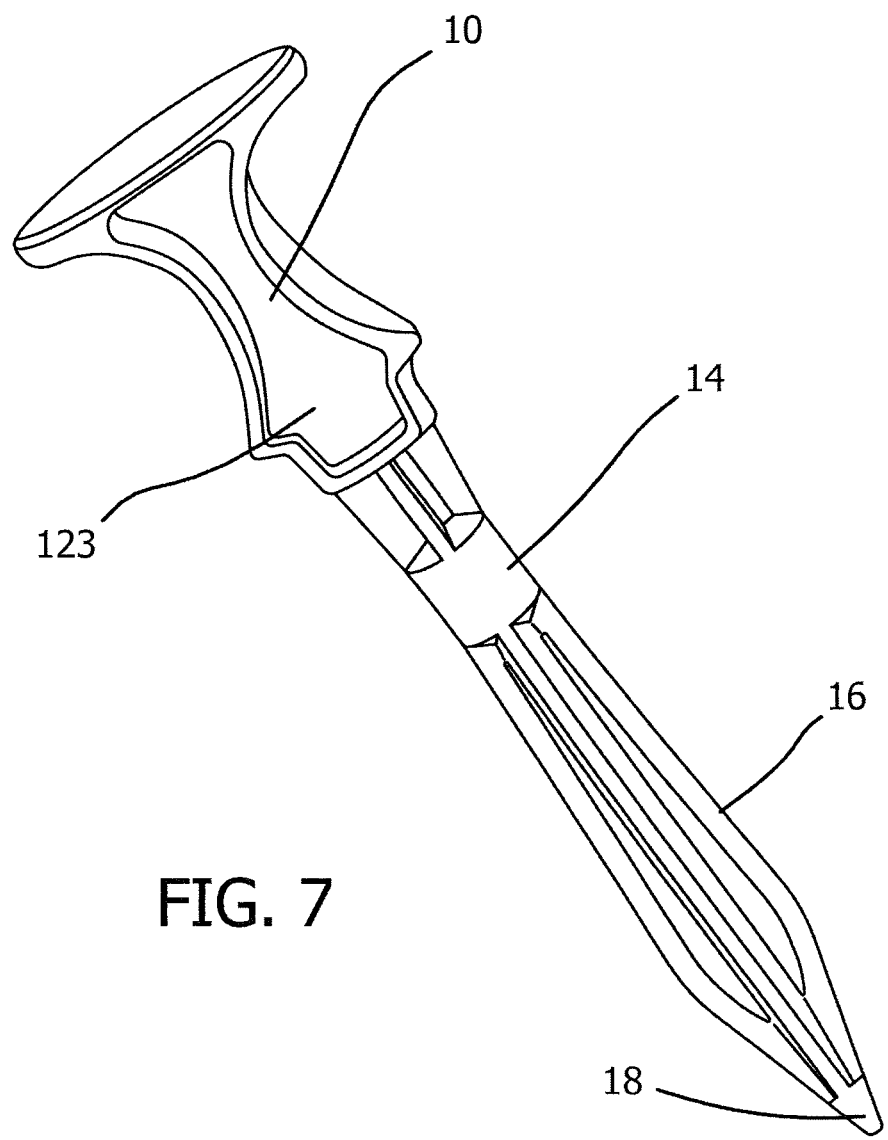
FIG. 7 is a perspective view of another embodiment of an obturator in accordance with various embodiments of the present invention.
Figure 8:
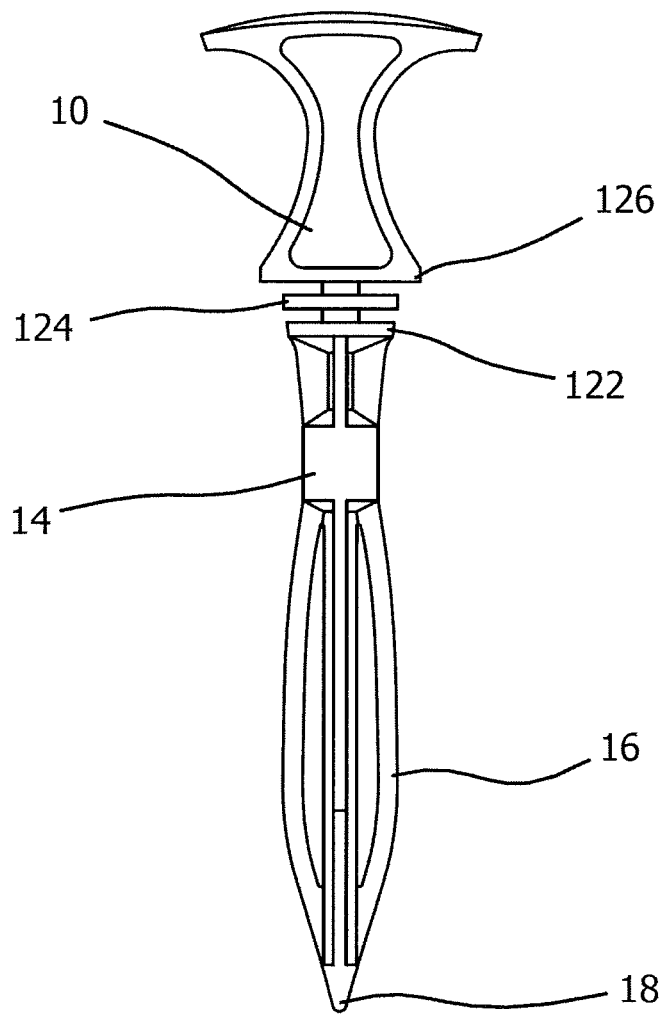
FIG. 8 is a side view of another embodiment of an obturator in accordance with various embodiments of the present invention.

In FIG. 6, the depth limiter or stepped portion 121 may be more pronounced or have a similar geometry as the ribs 16. In one embodiment the depth limiter may includes ribs. As such, the ribs of the depth limiter are readily manufactured similar to the compressible portion. The ribs of the depth limiter in one embodiment provide one or more expanded portions to limit the insertion of the obturator through a smaller sized trocar while also allowing or not restricting further or greater advancement of the obturator into larger sized trocars. Additionally, in one embodiment, the obturator ensures the distal portion extending out from the trocar remains unchanged even though the trocar sizes are different. The depth limiter in one embodiment can extend or be incorporated into the handle 10 as shown for example in FIG. 7. Such an extension 123 of the handle 10 can ease manufacturing of the depth delimiter or stepped portion. In FIG. 8, the stepped or expanded portion includes a disc 124 or a similar middle portion between first and second expanded portions 122 and 126 or to replace one of the expanded portions. The disc 124 can be used to clearly define or indicate the stop insertion point of the obturator relative to specifically sized trocar and/or to reduce material costs. For example, a first range of specific sized trocars would have the obturator stop at the first expanded portion, a second range at the disc 124 and a third range at the second expanded portion. As such, a similar look and feel of the obturator with the trocar will be provided to the surgeon regardless of the size of the trocars or the different sizes of the trocars relative to the same obturator.

Figure 9A:
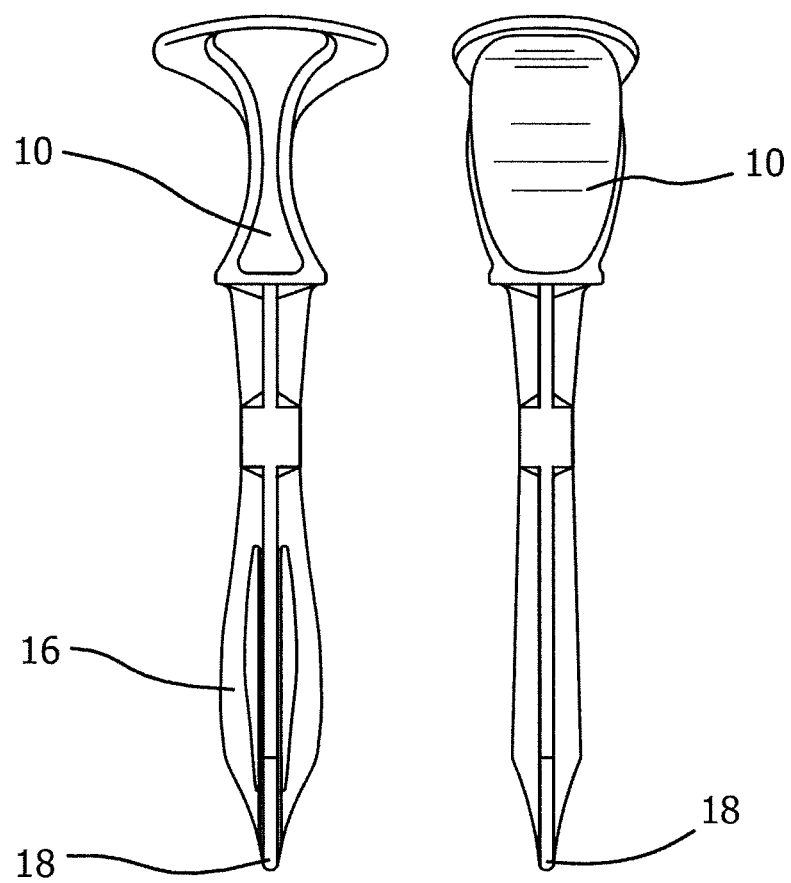
FIG. 9A illustrates side views of another embodiment of an obturator in accordance with various embodiments of the present invention.
Figure 9B:
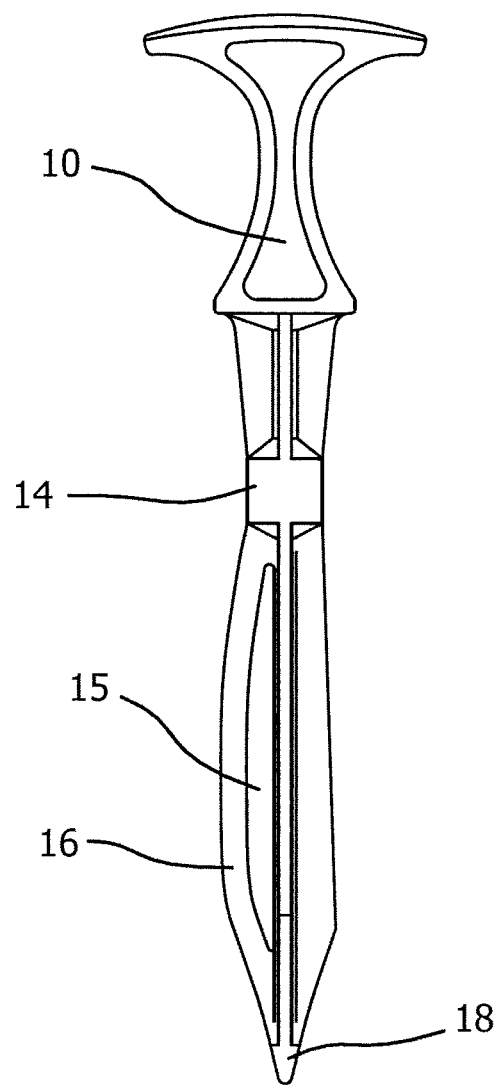
FIG. 9B is a side view of another embodiment of an obturator in accordance with various embodiments of the present invention.
Figure 10:
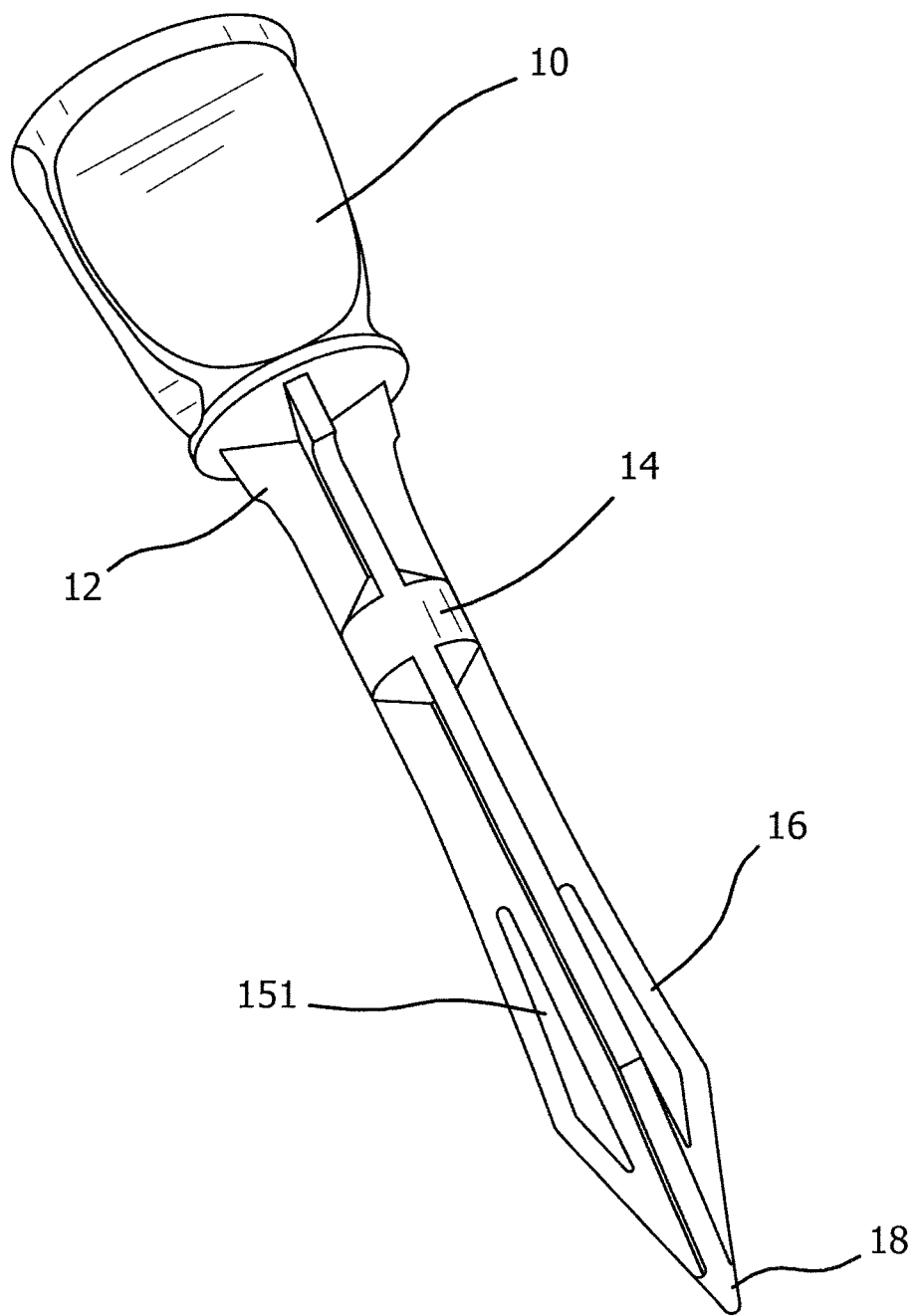
FIG. 10 is a perspective view of another embodiment of an obturator in accordance with various embodiments of the present invention.
Figure 11:
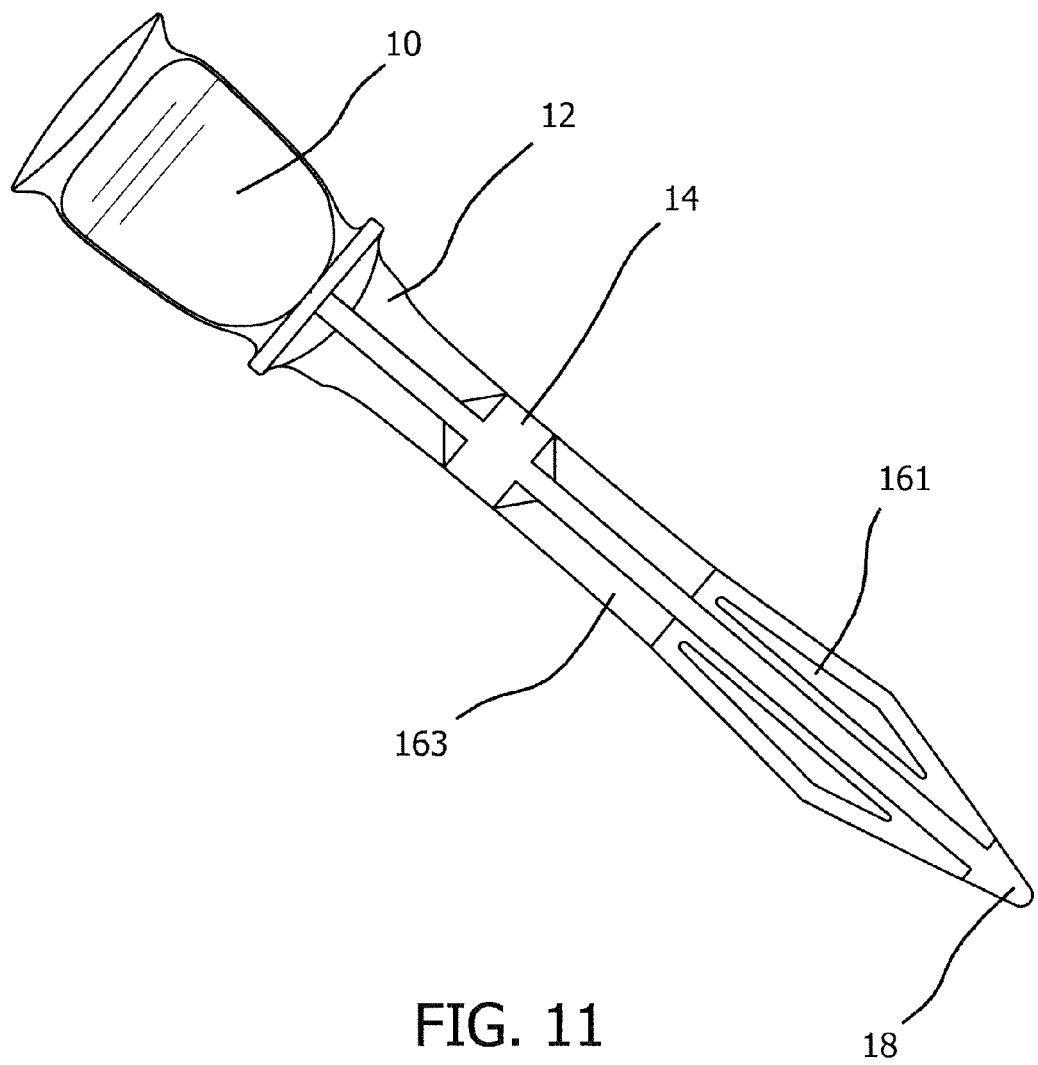
FIG. 11 is a perspective view of another embodiment of an obturator in accordance with various embodiments of the present invention.

In one embodiment, as shown in FIGS. 9A-9B, ribs 16 are positioned on symmetrically opposed sides of the obturator or only one rib, rib 16, is positioned on only one side to ease manufacturing. The single rib in one embodiment is larger or sized to occupy a larger portion of the inner diameter of the trocar relative to a plurality of ribs as the opposing portion of the shaft of the obturator is constant or unable to adjust in width or radially. The plurality of similarly sized and opposed ribs in one embodiment maintains a particular center or position of the tip relative to the distal end of the trocar. The rib or ribs remain compressible against the center shaft of the obturator to conform or mate with the small sized trocars and yet expandable to conform or mate with the large sized trocars thereby reducing or eliminating tip wobble. In FIG. 10, the gap between the ribs 16 are shortened to form gaps 151. In the illustrated embodiment, the compression or expansion of the ribs 16 may be limited by the shortened gaps 151 but also the tip or distal portion of the obturator could be strengthen. FIG. 11 illustrates the embodiment of the ribs or the portions thereof 161 that are separable from the shaft portion 163 of the obturator and thus assembled later to ease manufacturing of the components of the obturator. Additionally, different rib patterns or sizes, e.g., how much the ribs can expand or compress and be interchanged or swapped, can be utilized to increase the range of the options of providing a single obturator for multiple and different sized trocars. For example, a first rib set could be used for a specific range of sized trocars and a second different rib set could be used for a different specific range of sized trocars.

Figure 12A:
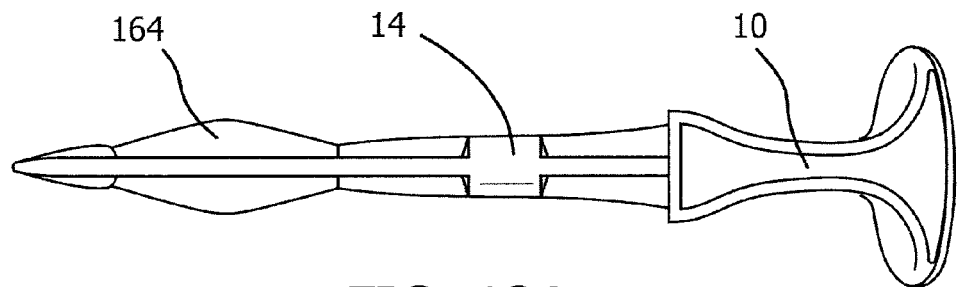
FIG. 12A is a side view of another embodiment of an obturator in accordance with various embodiments of the present invention.
Figure 12B:
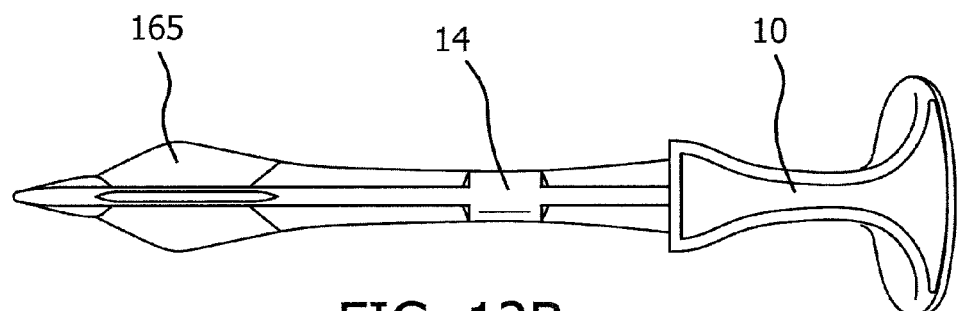
FIG. 12B is a side view of another embodiment of an obturator in accordance with various embodiments of the present invention.
Figure 12C:
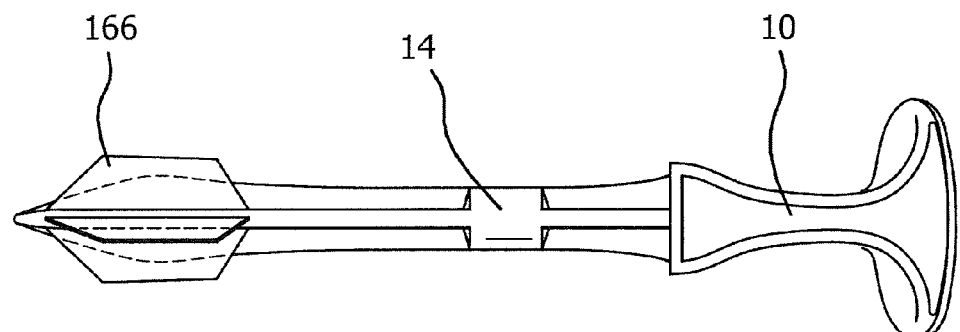
FIG. 12C is a side view of another embodiment of an obturator in accordance with various embodiments of the present invention.

In FIGS. 12A-12C, embodiments of flaps or leaves included with the obturator shaft in place of or to further enhance the ribs of the obturator to conform to different sized trocars are shown. The flaps or leaves are compressible in one embodiment and thus fold or spiral against the center shaft of the obturator when the obturator is inserted into a small sized trocar. The flaps splay outward from the shaft of the obturator to conform the inner diameter of larger sized trocars. In FIG. 12A, the flaps 164 are used instead of the ribs 16 and extend from the center shaft and FIG. 12B, the flaps 165 extend from raised portions along the center shaft of the obturator. In FIG. 12C, the flaps 166 are disposed between the raised portion and in one embodiment extend from or are disposed between ribs of the obturator.

In one embodiment, a separate sleeve or insert is fitted against the outer surface of the obturator to adjust and thereby conform to different sized trocars. As such, in FIG. 13, ribs 171 extend from a circular retainer 172 attachable to the tip or near the tip of the obturator. The ribs 171 in an expanded or initial state conforms to a large sized trocar and in a compressed state conforms or defines a diameter thereof of small or smaller sized trocars. In FIG. 14, a rib sleeve 173 includes ribs 174 and is attachable to the shaft of the obturator. The ribs of the rib sleeve are compressible and expanded to conform to the diameters of the various sized trocars.

In one embodiment, a elastic taper similar to the rib sleeve 173 with or without ribs is provided coupled to a proximal end of an inner shaft of the obturator, extending about the inner shaft and having a free end near a distal end of the inner shaft. The inner shaft connects the tip and an outer shaft of the obturator. In one embodiment, a diameter difference between the inner shaft and the outer shaft accommodates the taper when compressed against the inner shaft. The elastic semiconical or taper is radially compressible such that the taper in contact with an inner diameter of trocar moves towards the central shaft of the obturator with the central shaft including the inner and outer shafts. The taper in an expanded or initial state conforms to a large sized trocar and in a compressed state conforms or defines a diameter thereof of small or smaller sized trocars.

In one embodiment, the taper or sleeve is an elastic membrane or capsule that is filled with air, fluid or some other fillable material and in a filled or initial state conforms to a large sized trocar and in a compressed state conforms or defines a diameter thereof of small or smaller sized trocars. The tip of the trocar is offset, twisted or is designed to traverse tissue without cutting. The tip in one embodiment is arranged to move along overlapping and perpendicular tissue planes without cutting. The taper or sleeve coupled to the tip conforms to the distal end of the trocar whether the trocar is a large sized trocar or a small or smaller sized trocar and thereby prevents coring of tissue and maintaining the benefit of a particular tip. For example, the maintenance of the tip a specific distance from the distal end of the trocar ensures visibility; ensures tip cutting (blade clearance) and/or ensures gas pathway clearance. In one embodiment, the elastic taper is included with the ribs. In such embodiments, the elastic taper covers the ribs or portions thereof and act as a mechanical reinforcement to the elastic taper. In accordance with various embodiments, additional mechanical reinforcement can be provided via scaffolding, lattices, compressible material or the like to enhance or adjust the compressibility and/or expandability of the adjustable portion of the obturator.

Figures 1, 2, 15:
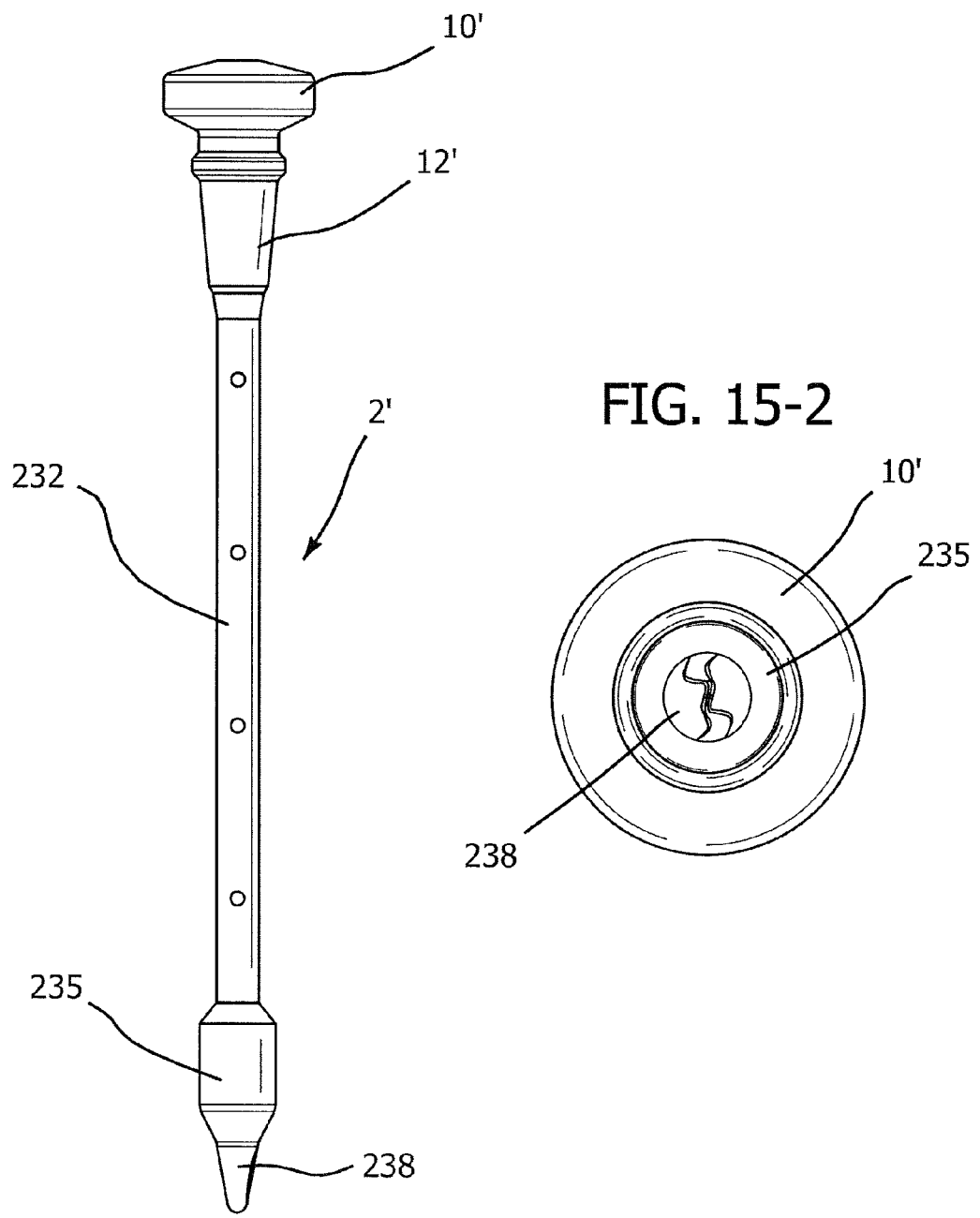
FIG. 15-1 is a side view of another embodiment of an obturator in accordance with various embodiments of the present invention.
Figures 3, 15:
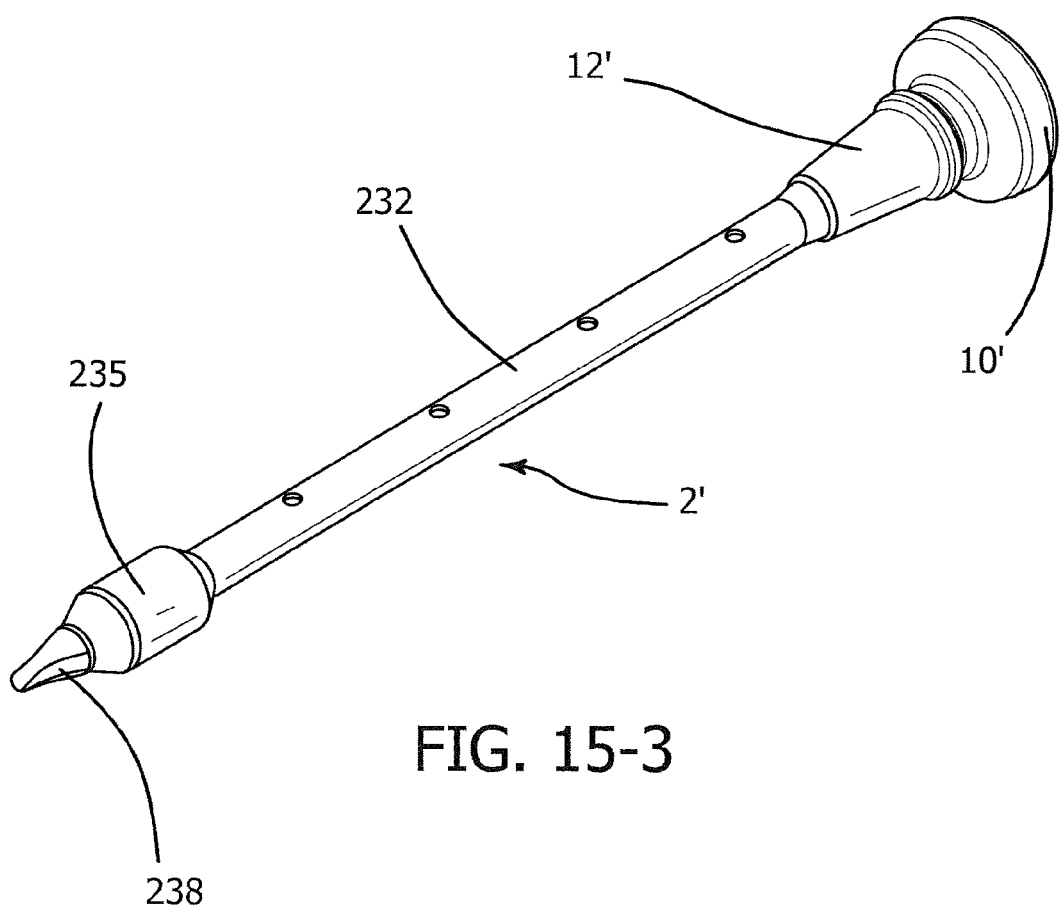
Figures 4, 15:
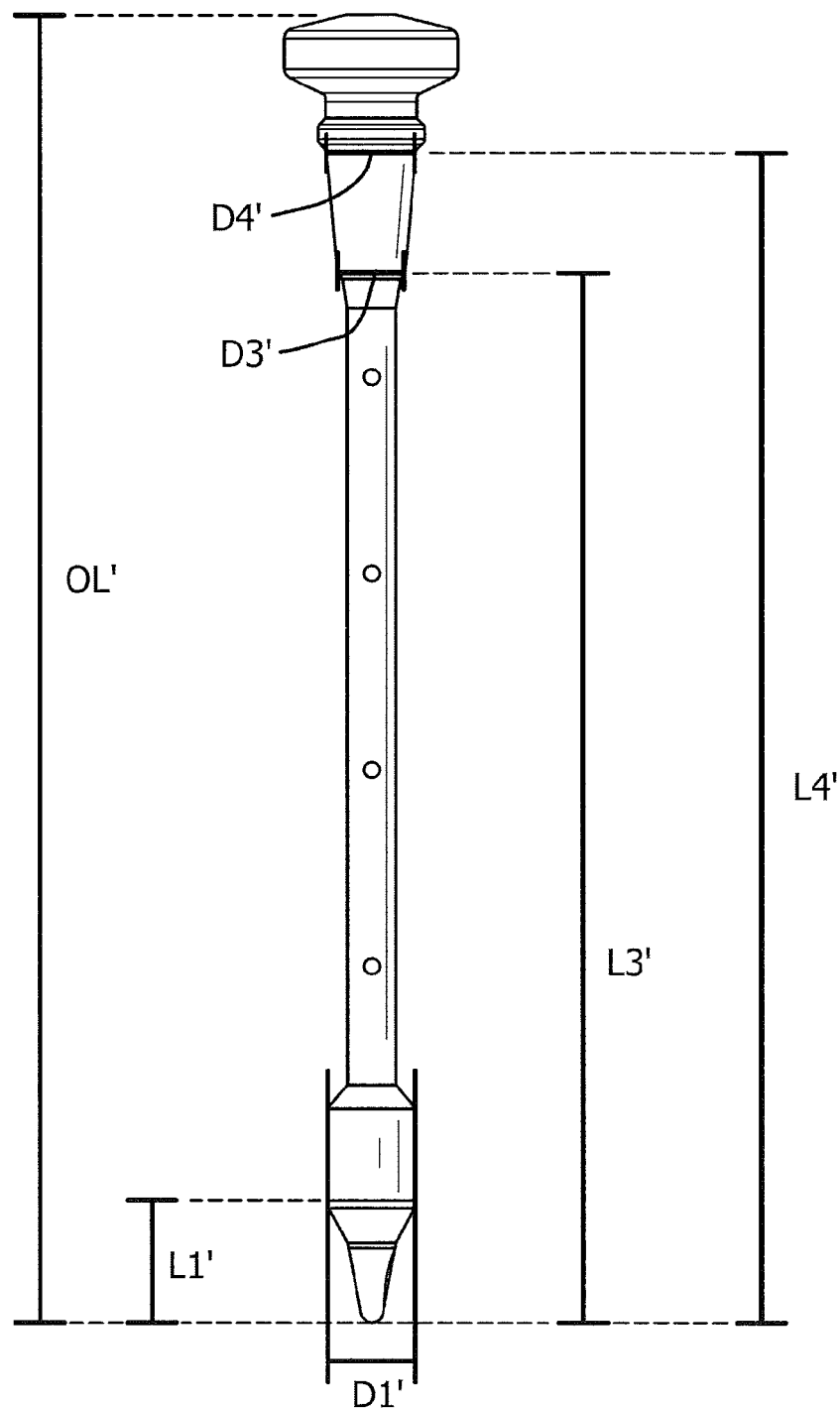
Figures 5, 15:
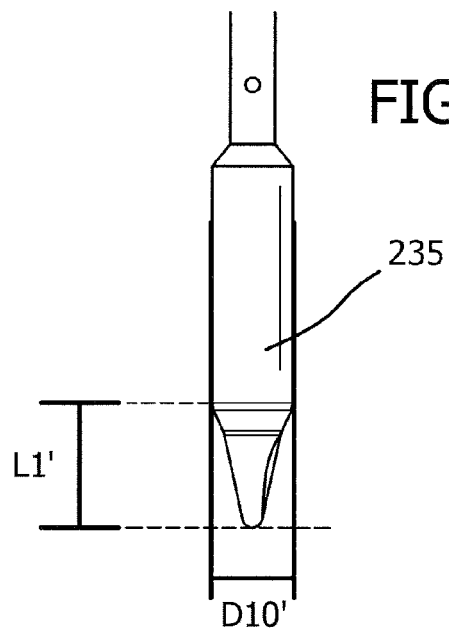
Figures 14, 15:
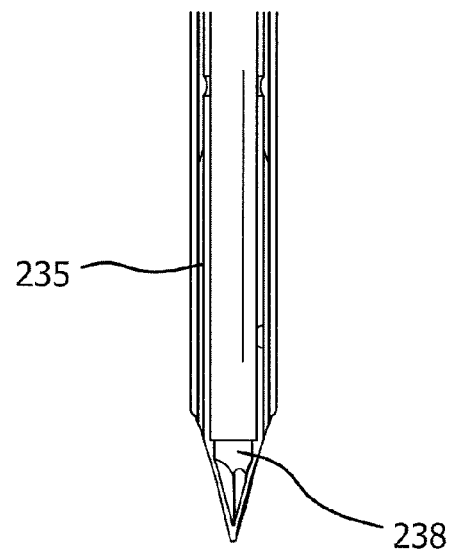
FIG. 14 is a side view of another embodiment of an obturator in accordance with various embodiments of the present invention.
Figure 15:
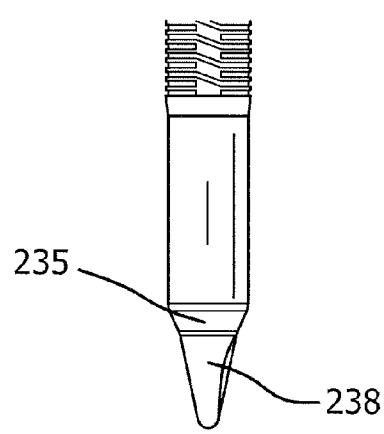
Figures 10, 15:
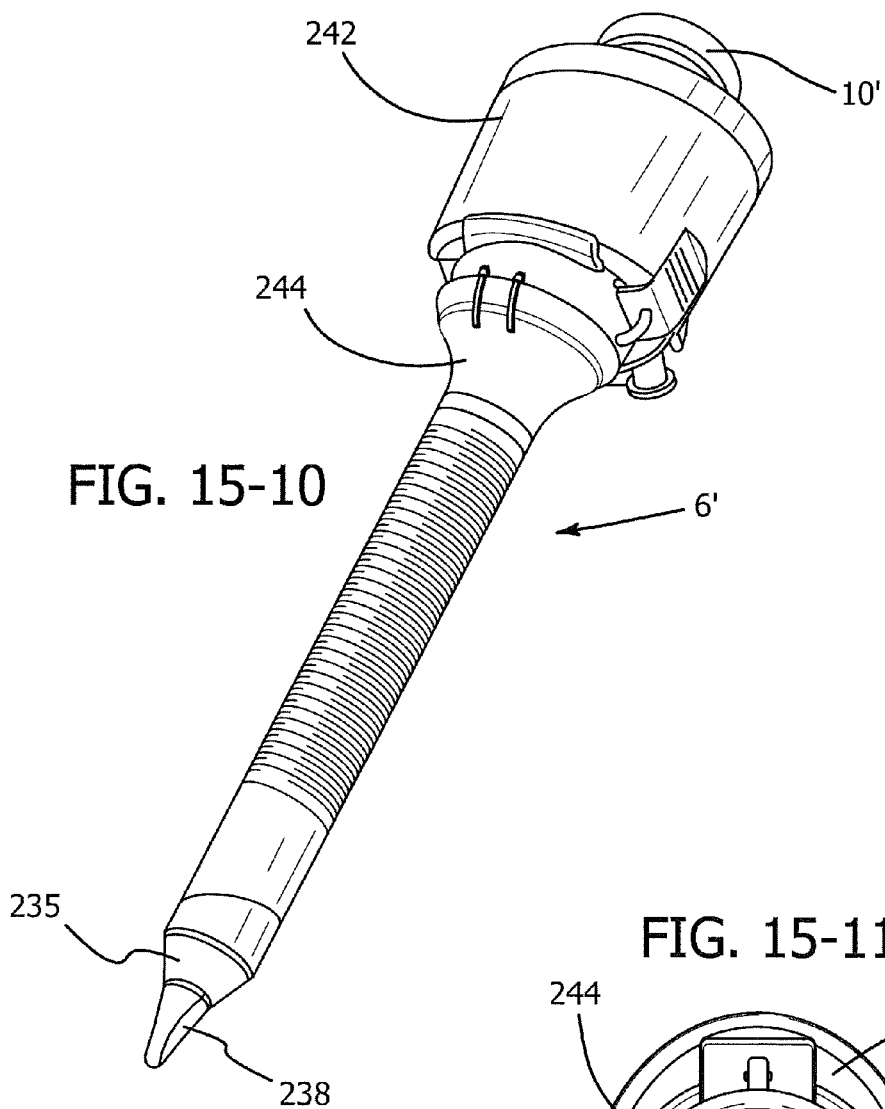
Figures 11, 15:
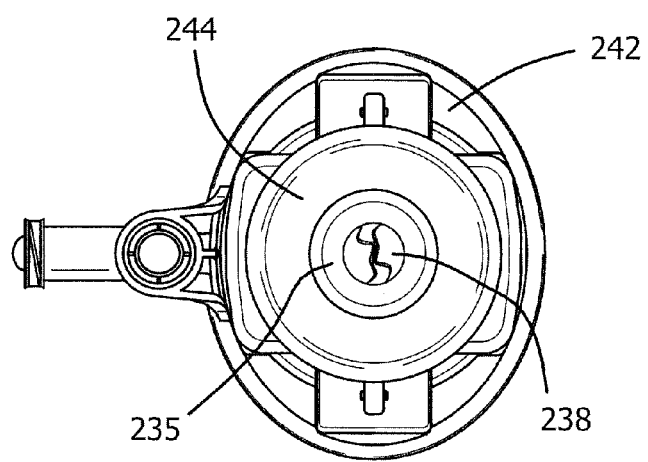
Figures 12, 15:
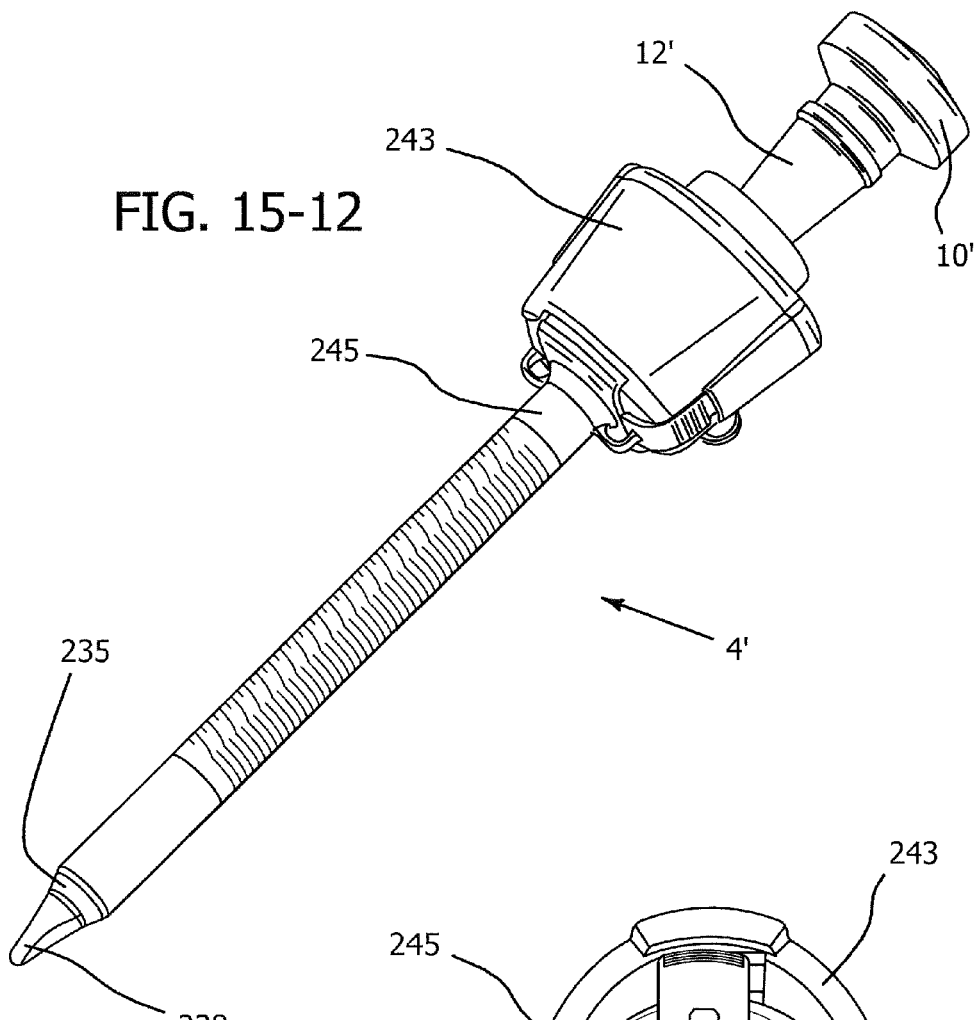
Figures 13, 15:
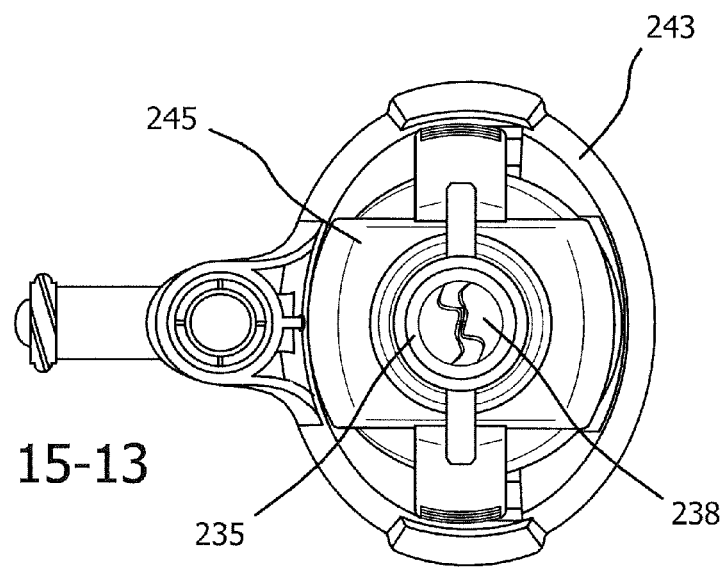
FIG. 13 is a side view of another embodiment of an obturator in accordance with various embodiments of the present invention.

Referring now to FIGS. 15-1 to 15-15, in which an adjustable obturator with a compressible sleeve is described in detail in relation with various sized trocars. It should be appreciated that the details provided are exemplary and can be applicable to other various sized trocars not explicitly shown or described and likewise other obturators or combinations of embodiments and features or aspects of various embodiments or combinations of embodiments described can also be applicable to the various sized trocars described herein and other similar trocars not explicitly shown or described. A compressible sleeve 235 in one embodiment is bulbous and made of compressible material incorporated with or connectable to the shaft 232. The compressible sleeve 235 is radially compressible such that the sleeve 235 in contact with an inner diameter of a trocar moves towards the shaft or central axis of the obturator. The sleeve 235 in an expanded or initial state conforms to a large sized trocar and in a compressed state conforms or defines a diameter thereof of small or smaller sized trocars. The tip 238 is offset, twisted or is designed to traverse tissue without cutting. The tip in one embodiment is arranged to move along overlapping and perpendicular tissue planes without cutting tissue. The sleeve 235, positioned at the tip, conforms to the distal end of the trocar whether the trocar is a large sized trocar or a small or smaller sized trocar to fill in or avoid undercuts or spacing between the distal open end of the trocar and the tip of the obturator to thereby prevent coring of tissue and maintaining the benefit of a particular tip. For example, the maintenance of the tip a specific distance from the distal end of the trocar ensures visibility; ensures tip cutting (blade clearance) and/or ensures gas pathway clearance. In one embodiment, the compressible sleeve is made of open-cell foam, memory foam or the like. In various embodiments, the compressible sleeve is preformed and/or provides no convention to operationally inflate, fill or externally adjust the compressive sleeve thereby avoiding potential operational and manufacturing complexities and difficulties.

In one embodiment, the obturator 2' in an initial expanded or non-compressed state defines a diameter and/or width D1' that is equal to or greater than the inner diameter of the largest cannula, e.g., cannula 244, to be used with the obturator. In a separate state or condition, the obturator defines or delimits a diameter and/or width D10' that is equal to or greater than the inner diameter of the smallest cannula, e.g., cannula 245, to be used with the obturator. This second defined diameter D10' is smaller than the diameter D1'. The obturator in various embodiments may have various other states or conditions between these two states or conditions in which the obturator defines or delimits a diameter and/or width that smaller than the inner diameter of the largest cannula, e.g., cannula 244, to be used with the obturator (or diameter D1') and larger than the inner diameter of the smallest cannula, e.g., cannula 245, to be used with the obturator.

The overall length OL' of the obturator remains constant. The stepped portion or depth limiter 12' in one embodiment defines or includes one or more expanded portions. For example, a first expanded portion is positioned a first length L3' and a second expanded portion is positioned a second length L4' both measured relative to the tip or distal most portion of the obturator to the respective expanded portions. In one embodiment, the lengths are measured relative to a distal portion of the obturator that substantially equals or corresponds to the distal end of one or more of the various sized trocars through which the obturator extends there through when fully inserted into the trocar or trocars. The first and second lengths are smaller than the overall length of the obturator.

In various embodiments, the first and/or second expanded portions 125, 127 are positioned ahead of or adjacent to the handle portion 10' of the obturator 2' and in various embodiments the first and/or second expanded portions are blended into or formed as part of the handle portion 10' of the obturator 2'. As such, the handle portion 10' defines a first and/or second expanded portion. In one embodiment the depth limiter is tapered or graduated having or defining a first distal diameter, e.g., diameter D3', and graduating, tapering or having steps to one or more larger sections, portions, flanges or abutments having or defining one or more larger proximal diameters, e.g., diameter D4'.

The first expanded portion 125 abuts against the cap or proximal portion of the valve housing 243 but does not abut against the cap or proximal portion of the valve housing 242 of a trocar larger than the trocar with the valve housing 243. As such, the first expanded portion 125 passes the cap or proximal portion of a larger or largest trocar while the second expanded portion 127 abuts against the cap or proximal portion of the trocar of the larger or largest trocar when the obturator is inserted into the trocar.

The first expanded portion of obturator 2' as illustrated defines a first diameter D3' that is smaller than the diameter D4' defined by the second expanded portion. The first diameter D3' equals or is larger than the diameter of D11' of the proximal portion or cap of trocar 4' and trocar 4' for exemplary purposes represents the smallest trocar to be used with the obturator. As such, when the obturator is inserted into the trocar, the first expanded portion contacts the cap or outer surface of the cap of the trocar to prevent further distal or insertion of the obturator into the trocar. The first diameter D3' is however smaller than the diameter of D12' of the proximal portion or cap of trocar 6' and trocar 6' for exemplary purposes represents the largest trocar to be used with the obturator or at least larger than the first trocar. When the obturator is inserted into trocar 6', the first expanded portion does not contact the cap or outer surface of the trocar and thus travels further into the trocar 6'. The second expanded portion of the obturator as illustrated defines a second diameter D4'. The second diameter D4' is greater than the first diameter D3' and the diameter D11' of the trocar 4'. The second diameter D4' equals or is larger than the diameter of D12' of the proximal portion or cap of trocar 6'. Thus, when the obturator continues to be inserted into the trocar 6', the second expanded portion contacts the cap or outer surface of the cap to prevent further distal movement or insertion of the obturator into the trocar 6'. Accordingly, the obturator is allowed to or is not restricted from advancing farther into a trocar with a larger inner diameter than a trocar with a smaller inner diameter.

In one embodiment, the portion of the obturator extending out from the distal end of the smallest cannula with the obturator fully inserted there through and the portion of the obturator extending out from the distal end of the largest cannula with the obturator fully inserted there through are the same. As such, the same tip geometry (e.g., shape, dimensions, length, width and/or diameter) is provided by the obturator even though different length trocars or cannulas are used. For example, in the illustrated embodiment, the distal length L1' of the obturator 2' that would extend out from the distal end of trocars 4' and 6', for example, remains the same even with the overall lengths of the trocars being different. The tip of the obturator in one embodiment with the obturator fully inserted within various sized trocars has or defines an outer surface or circumference that is flushed with the distal end of the trocar. As provided in the illustrated embodiment, the length of trocar 4' is smaller than the length of the trocar 6' with both trocar lengths being smaller than the overall length of the obturator 2'.

In one embodiment, ribs 16 are included with the compressible sleeve with the sleeve covering the ribs 16. In other embodiments, the compressible sleeve includes slots or opening through which the ribs 16 are exposed or protrude out from the sleeve. In other various embodiments, the compressible sleeve is a plurality of individual sections or wedges that fill in portions between the ribs. In one embodiment, the compressible sleeve is porous and provides a gaseous pathway through the compressible sleeve and out the distal end of the trocar. In one embodiment, the porous compressible sleeve is used for initial insufflation and replaced with a non-porous compressible sleeve when a gaseous pathway is not desired. In accordance with various embodiments, the compressible sleeve or portions thereof is preformed into a specific shape and/or dimension to conform to the obturator tip and the various diameter sizes of the distal ends of the various sized trocars.

In the illustrated embodiment and applicable to various other embodiments, the distal portion of the compressible sleeve can be tapered or more resilient, e.g., made of a material more resilient or compressible than other portions of the sleeve, to facilitate insertion of the obturator into the various sized trocars by reducing friction or otherwise minimizing contact of the distal portion of the compressible sleeve with the inner diameter or portion of the trocar including for example various seals, valves, housings and cannulas. Similarly, in the illustrated embodiment and applicable to various other embodiments, the proximal portion of the compressible sleeve can be tapered or more resilient, e.g., made of a material more resilient or compressible than other portions of the sleeve, to facilitate removal or withdrawal of the obturator from the various sized trocars.

Figure 16:
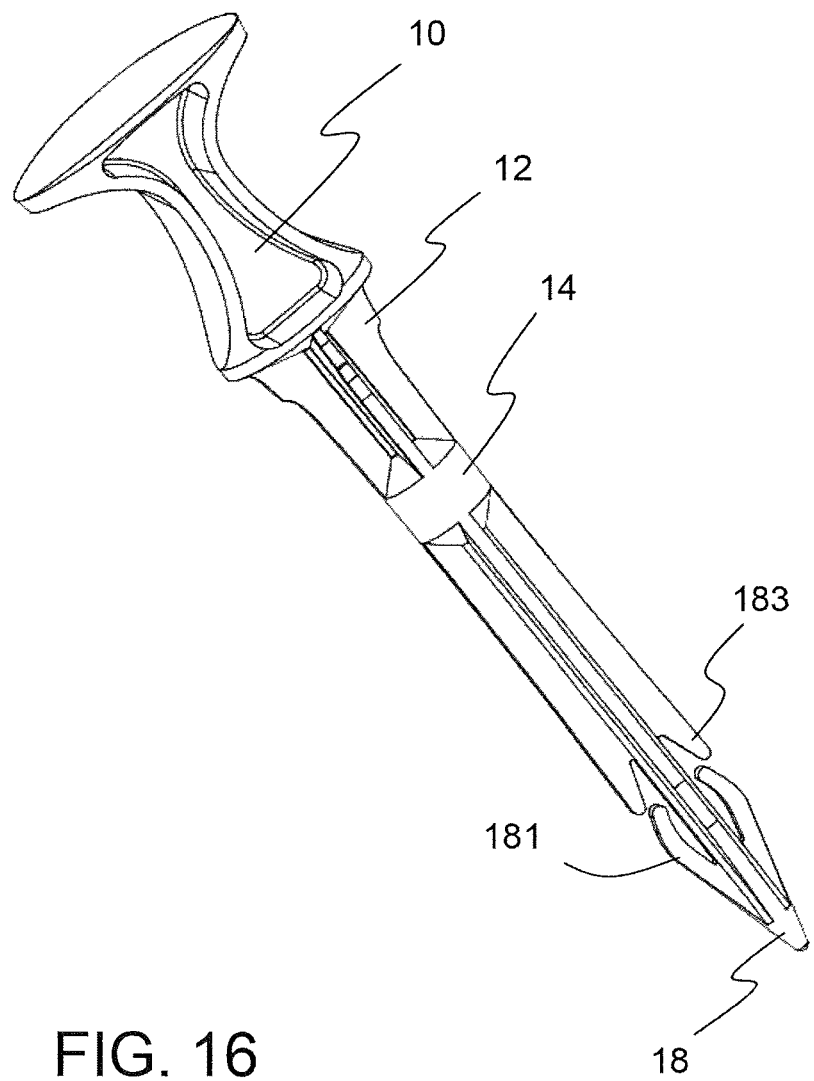
FIG. 16 is a perspective view of another embodiment of an obturator in accordance with various embodiments of the present invention.
Figures 17A, 17B:
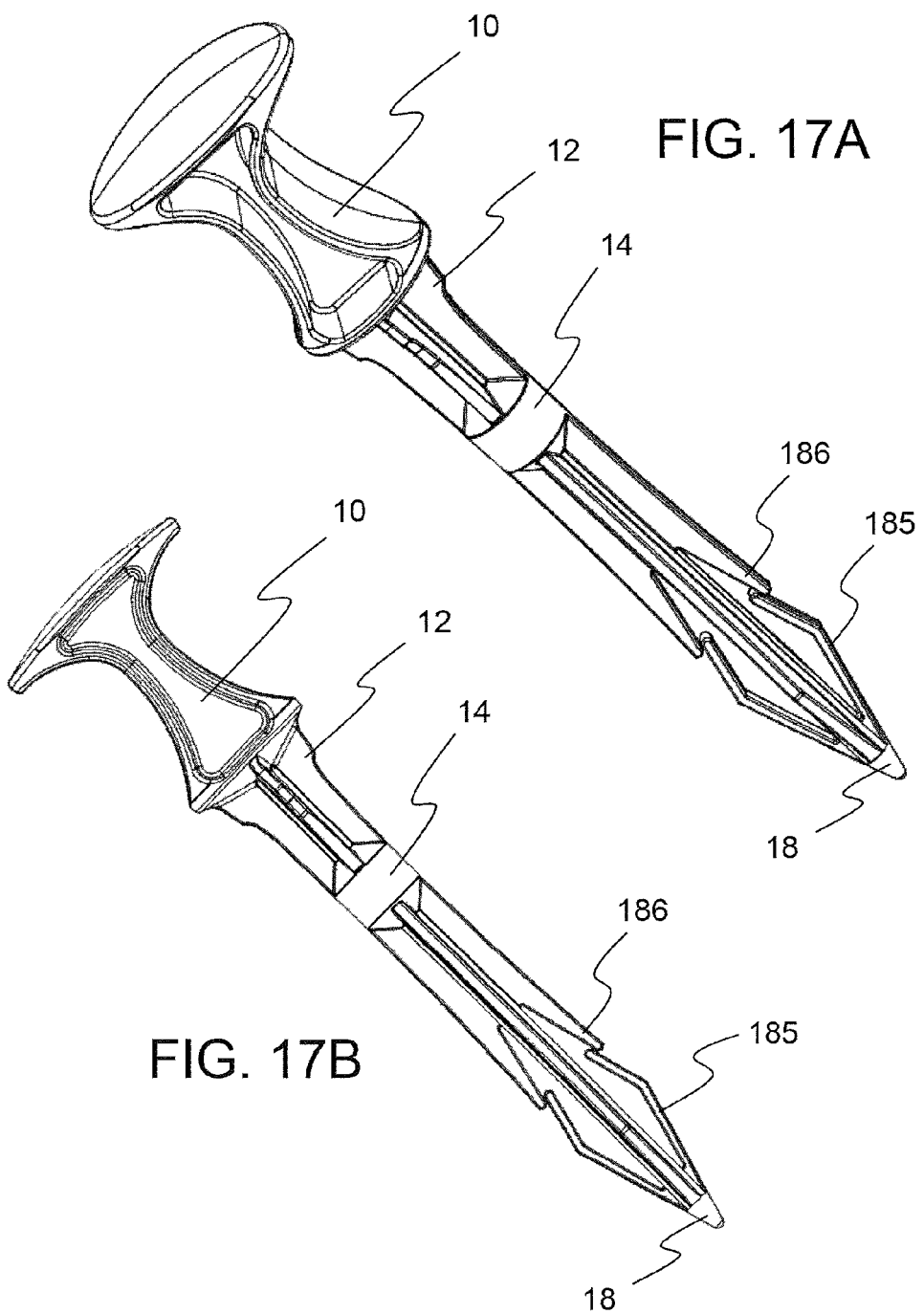
FIG. 17A is a perspective view of another embodiment of an obturator in accordance with various embodiments of the present invention.
FIG. 17B is a side view of an embodiment of an obturator in accordance with various embodiments of the present invention.
Figure 18:
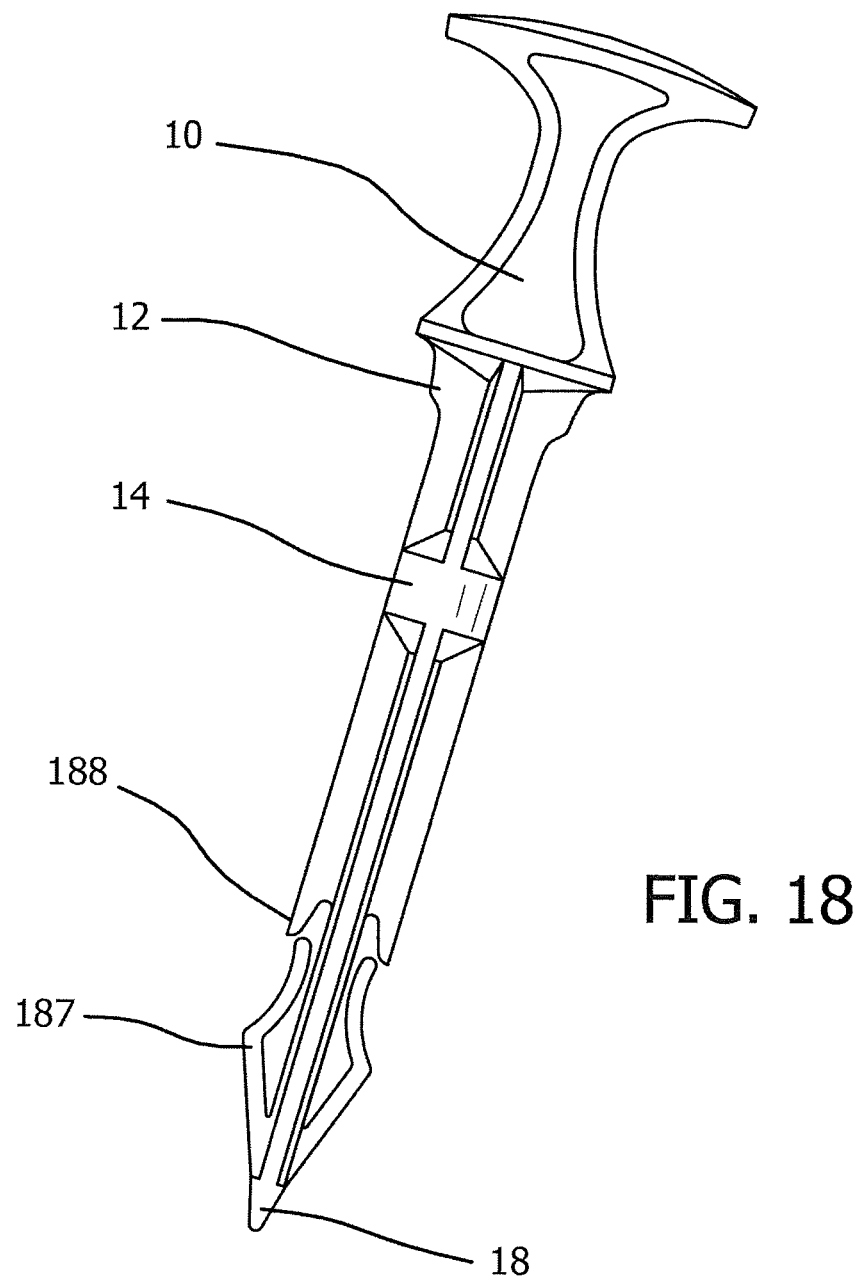
FIG. 18 is a perspective view of another embodiment of an obturator in accordance with various embodiments of the present invention.
Figure 19:
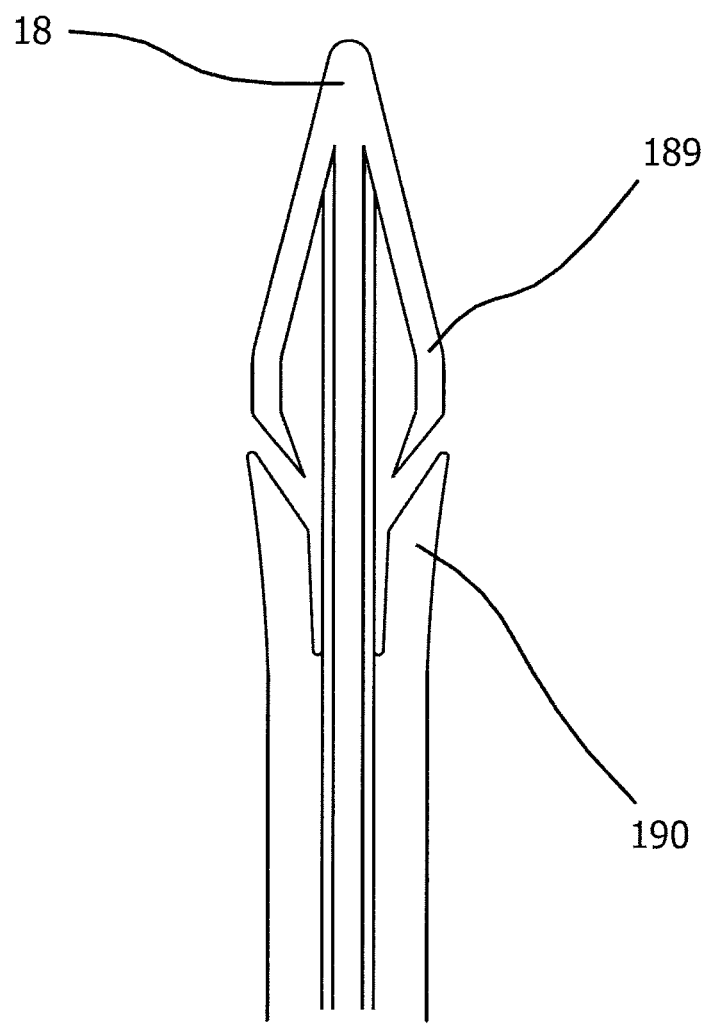
FIG. 19 is a side view of a distal portion of another embodiment of an obturator in accordance with various embodiments of the present invention.

Referring now to FIGS. 16-19, gapped or opened ribs are shown along an obturator. In FIG. 16, the ribs 181 are curvilinear and extend up to a gap portion separating the proximal end of ribs 181 with a sectioned or prong portion 183 of the obturator. The gapped ribs can increase compressibility or expandability of the ribs and reduce overall diameter size of the obturator. The gapped ribs 185, 187 with respective prong portions 186, 188 as shown in FIGS. 17A-B and 18 are more pronounced, peaked and/or curved and can further increase compressibility or expandability of the ribs. The prongs capture the proximal ends of the gapped ribs to prevent the ends from splaying and thus snagging against an inner surface or portion of the trocar. FIG. 19 illustrates ribs 189 with prongs 190 which are similar to the ribs 16 previously described with ribs 189 having a similar shape and size as the ribs 16 with a gap formed or cut out along the rib to form the prongs 190.

In various embodiments, the obturator includes a tip skirt coupled to the shaft at the distal end of the obturator and near the tip. The tip skirt fills in spacing between the tip of the obturator and the distal open end of the trocar. As such, the tip skirt provides a smooth, uniform and/or consistent transition from the obturator tip to the periphery of the distal open end of the trocar. Therefore, regardless how long the trocar is relative to the obturator or how wide or large the diameter of the distal open end of the trocar is relative to the obturator, a smooth, uniform and/or consistent transition from the obturator tip to the periphery of the distal open end of the trocar is maintained. In accordance with various embodiments, the tip skirt differs from the compressible portions, such as the elastic taper, in that the tip skirt does not specifically conform to the various inner diameters of the various sized trocars, but conforms specifically to the geometry of the distal open end of the trocar, e.g., the various shapes and diameters of the distal open end of the various sized trocars.

In accordance with various embodiments, the tip is retractable or movable proximally when the ribs 16 are compressed. In one embodiment, the tip is extendable or movable distally when the ribs 16 are not compressed or under less compression. In one embodiment, a tip skirt is released or expanded when the ribs are not compressed or under less compression and/or the tip is extended and/or in one embodiment the tip skirt is captured, restricted or compressed when the ribs are compressed and/or the tip is retracted.

In accordance with various embodiments, the obturator includes a visual pathway providing visualization before, during and/or after tissue traversal of the obturator through and into the patient via an endoscope or the like connected or inserted through the shaft of the obturator. The tip or portions thereof may be transparent and/or include mirrors, windows or lens to enhance or optimize visualization. In accordance with various embodiments, the obturator may only include or also include a gaseous or fluidic pathway to provide for instance insufflation and/or visualization. For example, the tip may include one or more vents or openings allowing gas to pass from the proximal end of the obturator outside the patient and connected to a gas source through the obturator shaft and out the opening in the tip of the obturator.

In accordance with various embodiments, spacing between the ribs and the tip relative to the distal open end of the trocar provides one or more pathways or channels allowing gas to pass from the proximal end of the obturator along the outer surface and/or through the shaft of the obturator and out a space between the ribs, tip and distal open end of the trocar. In one embodiment, the space is sufficient to allow gas flow but not significant to provide an undercut or space that can cause tissue coring or trauma. In accordance with various embodiments, the tip of the obturator has cutting edges or blades and/or includes one or more shields to cover the cutting edges or blades when not in use. The compressible portion such as the ribs in one embodiment may be incorporated with the shield or placed adjacent to the shield. The compressible portion engaging with the various sized inner diameters of the respective various sized trocars ensure a stable (wobble-free) obturator regardless of trocar size thereby providing stable cutting, separating, insufflating and/or visualization. In accordance with various embodiments, the compressible portions also provides for a static or constant centering or positioning of the tip or center portion of the tip as desired by the particular tip relative to the distal end of the trocar and prevents potential tissue coring or trauma.

In accordance with various embodiments, the obturator is a monolithic structure and in one embodiment the obturator is made from polycarbonate or polyester. The obturator is arranged such that it does not scrape the inner wall of the trocar or cannula portion of the trocar. The compressible portions of the obturator in accordance with various embodiments is sufficiently strong to contact and be flush with various sizes of the inner diameters of various sized trocars and sufficiently weak to not introduce scrapping, strain or added friction against the inner diameters of the various sized trocars to prevent damage or undue forces or interactions that increase insertion and/or removal force, e.g., preventing insertion of the obturator into the trocar or removing the obturator out of the trocar. The compressible portions of the obturator in accordance with various embodiments is also sufficiently compressible to adjust to various sized trocars for multiple uses such that the portions don't snap, fracture or break after continued use. The compressible portions in various embodiments are not twistable, bendable or able to change along the curvature of the trocar. The compressible portions in one embodiment is rigid axially and compressible only in a radial direction towards the center shaft of the obturator. In various embodiments, the compressible portions surround a center shaft of the obturator in which the center shaft is entirely rigid, not twistable and/or not bendable.

In accordance with various embodiments, the compressible portion, shaft and tip together form a monolithic structure. The core seal and/or depth limiter may be made of polycarbonate, polyester and/or made of the same material as the elongate shaft. In various embodiments, the core seal, depth limiter, shaft and tip, individually, all together or in various combinations thereof, are made of a non-elastomeric material and/or are not adjustable, adaptable or compressible. In accordance with various embodiments, the obturator is not insertable into a vessel or urinary tract, the obturator being not bendable, flexible or too hard to traverse the vessel or urinary tract.

In accordance with various embodiments, the compressible portions of the obturator are non-inflatable. In one embodiment, the compressible portion further comprises at least one rib having an initial state being fully extended and delimiting a first diameter and the at least one rib having a compressed state delimiting a diameter about half to about fifteenth the size of the first diameter. In one embodiment, the tip has a hardness to penetrate the surgical access device and in one embodiment the tip has a hardness to penetrate the body wall. In accordance with various embodiments, the shaft may be rigid non-bendable and/or solid and not hollow. In one embodiment, the compressible portion may be solid and not hollow and/or the handle may be solid and not hollow with no cavities or apertures.

It should also be appreciated that the obturator may have provided with the depth limiter or stepped or expanded proximal portion without the compressible portion, e.g., ribs, and vice versa. It should also be appreciated that the core seal could be incorporated or extended into the compressible portion, the depth limiter or both. It should also be appreciated that the core seal could be tapered, conical or shaped or dimensioned in a manner not cylindrical but able to seal against the aperture of the instrument seal used for both the largest trocar or cannula and the smallest trocar or cannula and various sizes between the largest and smallest trocars. It should also be appreciated that the obturator may have provided with the depth limiter and/or the compressible portion without the core seal.

In accordance with various embodiments, a surgical access device contacts the body and trocars are inserted through this access device. The obturator is inserted into the working channel of the cannula of the trocar and together they are pushed through the access device with a penetration or insertion force of sufficient magnitude to result in penetration through the access device. The access device in one embodiment is used to line and/or protect the incision or entry site into the patient's body.

Some of these access devices are introduced into regions that include a fluid or gas under pressure. For example, the pressure may be from a gas, such as an insufflation gas. As such, it is desirable to provide for the introduction of the surgical instrument into the cavity without permitting the escape of the pressurized fluid or gas. In some embodiments, trapped air, gas or fluid within the cannula or the pressure against the access device can cause resistance to the insertion of the obturator and trocar combination through the access device. Likewise, material or portions of the access device through which the adaptable obturator and trocar combination is inserted therethrough can also cause resistance to the insertion of the trocar through the access device. Accordingly, maintaining predictable insertion force and feel provided by the obturator in accordance with various embodiments can facilitate the insertion of the trocar into the access device. Thus, unintended stress experienced by the access device due to insertion of the trocar can be avoided.

Figure 20:
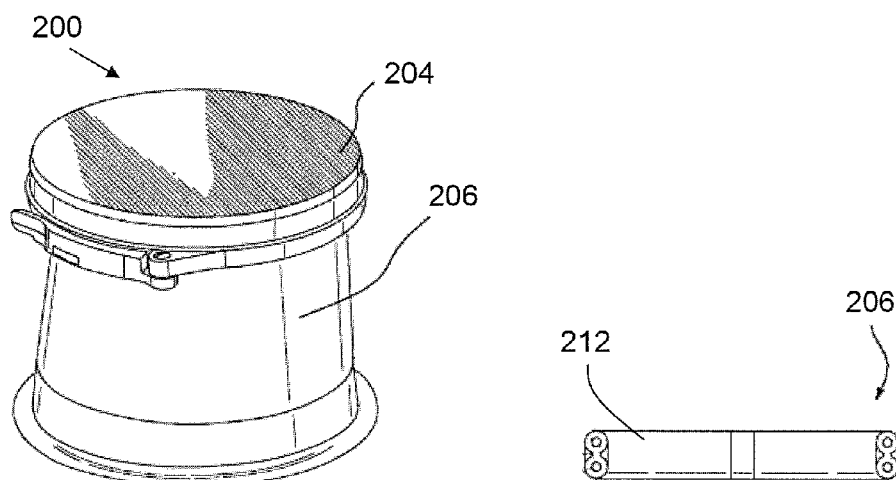
FIGS. 20-22 are perspective views of various embodiments of access devices in accordance with various embodiments of the present invention.
Figure 21:
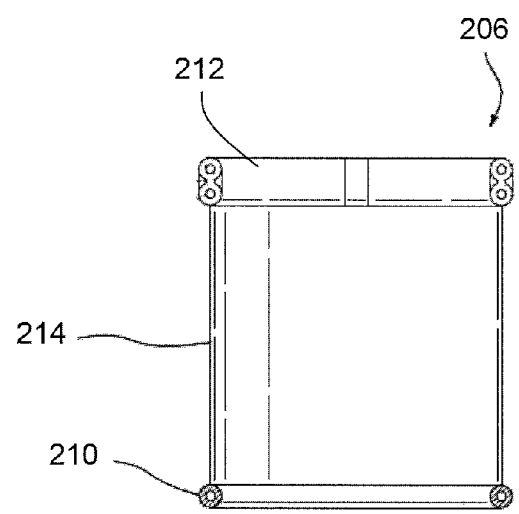
Figure 22:
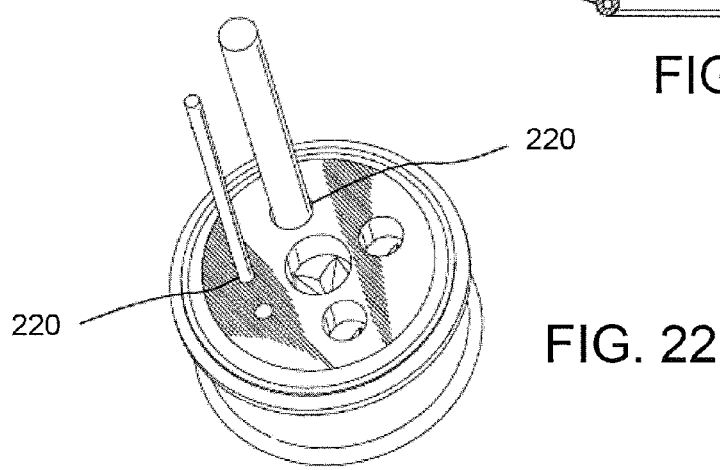

Examples of such access devices are illustrated in FIGS. 20-22 in which an access system 200 comprises a retractor or body wall liner 206 and a cap 204. The retractor or surgical wound retractor 206 is placed and/or positioned into, across, and/or through a surgical incision and/or body orifice to enlarge, reshape, and/or isolate the incision or body orifice. The cap provides an artificial body wall through which instruments and/or trocars access the interior of a patient's body, for example, a body cavity. This and other embodiments of access device systems are described in U.S. Patent Publication No. 2007/0088204 A1, the entire disclosure of which is hereby incorporated herewith by reference.

In one embodiment, the retractor 206 comprises an inner or distal ring 210, an outer or proximal ring 212, and a sleeve or retraction sheath 214 extending between and coupling the inner ring and the outer ring. The inner ring is flexible and compliant to be compressed and/or deformed for insertion through an incision and/or body orifice. When subsequently released within an associated body cavity, the inner ring substantially returns to its original shape or footprint.

A cap or cover used with or without the retractor seals the opening between the body cavity and the area outside the body cavity while providing access into the body cavity from outside the body cavity. In one embodiment, the cap releasably and sealingly couples to the outer ring of the wound retractor. The cap comprises a cap ring dimensioned and configured for coupling to the outer ring of the wound retractor and a pad coupled to the cap ring. Embodiments of the cap provide an artificial body wall with consistent properties compared with a natural body wall, for example, thickness, compliance, rigidity, uniformity, and the like.

In some embodiments, the pad comprises a gel. In some embodiments, the gel pad does not comprise any preformed access channels therethrough, for example, for instrument access. Trocars and/or instruments may be inserted directly through the gel pad, puncturing the gel pad, and thereby creating access channels or portions in the gel pad. Each access portion forms an instrument seal in the presence of an instrument inserted therethrough and a zero seal in the absence of an instrument inserted therethrough. The gel provides a gas tight seal around a variety of shapes and sizes of instruments inserted therethrough. Embodiments of the gel pad have a working diameter of from about 40 mm to about 120 mm, which is the diameter of a portion of the gel pad through which instruments and/or trocars may be inserted. Embodiments of the gel cap are typically from about 10 mm to 50 mm wider than the working diameter.

Accordingly, embodiments of the gel cap maintain pneumoperitoneum during multiple instrument exchanges and substantially prevent unintentional loss of pneumoperitoneum. Embodiments of the gel cap also provide substantially continuous access and visibility during surgery. Embodiments of the gel cap have a small profile for use in procedures with limited surgical space.

In some embodiments, the gel is an ultragel, which is characterized by an ultimate elongation greater than about 1000 percent and a durometer less than about 5 Shore A. Some embodiments of the ultragel comprising KRATON® and mineral oil exhibit an ultimate elongation exceeding about 1500 percent and improved sealing properties, for example, sealing with instruments of a wider size range than other seal materials. In some embodiments, the seals comprising ultragels also form zero seals when the instrument is removed therefrom. Accordingly, in some embodiments of seals comprising ultragels, a single seal is acts as both the instrument seal as well as the zero seal.

Some embodiments of the gel pad comprise an elastomeric gel. Examples of such gels are described in U.S. patent application Ser. No. 10/381,220, filed Mar. 20, 2003, the disclosure of which is hereby incorporated by reference as if set forth in full herein. As discussed above, embodiments of the gel cap comprise no preformed access channels in the gel pad. In use, instruments may be inserted directly through the gel pad, thereby creating access channels through the gel pad. Each access channel created in the gel cap forms an instrument seal in the presence of an instrument passing therethrough because the gel provides a gas tight seal around a variety of shapes and sizes of instruments. When the instrument is removed from the gel pad, the channel created in the gel pad by the instrument closes to form a zero seal. In accordance with various embodiments, the gel is not susceptible to coring, tearing or damage provided by undercuts and/or spacing between the tip of the obturator and the distal end of the trocar. In one embodiment, spacing between the ribs and the tip relative to the distal open end of the trocar provides one or more enlarged pathways or channels allowing gas to pass from the proximal end of the obturator along the outer surface and/or through the shaft of the obturator and out a space between the ribs, tip and distal open end of the trocar for example to increase gas flow, reduce material and/or ease manufacturing but can cause tissue coring but not coring into an access system such as a gel pad.

Because the gel cap in various embodiments initially comprises no access channels, the surgeon is at liberty to determine the placement of instruments therethrough. Moreover, the surgeon has unlimited flexibility in the placement and repositioning of ports within the area of the gel cap, as well as the option of selecting different trocar sizes for different clinical procedures. Being detachable, the gel cap allows for the removal of large specimens. Once removed, the gel cap can be re-coupled for example to the outer ring of the wound retractor, thereby restoring the seal and allow the surgeon to re-insufflate the body cavity.

Moreover, embodiments of the gel are deformable without losing physical integrity, and while maintaining substantially gas tight instrument seals with any instruments extending therethrough, as well as gas tight zero seals for any access channels without any instruments extending therethrough. Accordingly, embodiments of the gel cap permit both translational or positional, and angular or pivotal "float" or degrees of freedom for the instruments passing through the gel pad. This float permits instrument motion both relative to the cap ring as well as relative to other instruments. In contrast, other single or limited port systems do not exhibit one or both translational or angular float for instruments.

In various embodiments of a gel cap, the gel cap comprises a plurality of access ports, seals, or sealing valves 220 disposed in or embedded in the gel pad. The lengths of the access ports in one embodiment are similar to the thickness of the gel pad, which is shorter than a length of a trocar inserted in the gel pad. The reduced length of the access port allows increased angular or pivotal motion for instruments extending therethrough, and also permits the use of curved and/or angled instruments. In the some embodiments, the access ports are substantially permanent or non-removable under the conditions under which the gel cap is used.

In some embodiments, the trocar or the cannula body of the trocar is comparatively short because the cannula body only traverses the gel pad, which has a known and consistent thickness, rather than a body wall. Accordingly, some embodiments of the cannula body are not more than about 2-times longer, about 1.5-times longer, about 1.2-times longer, or about 1.1-times longer than the thickness of the gel pad. In some embodiments, the cannula body is less than about 20 mm, about 10 mm, or about 5 mm longer than the thickness of the gel pad. In some embodiments, the cannula body is about as long as the gel pad is thick. In other embodiments, the cannula body has a different length, for example, a length typical for a cannula used for traversing a body wall. Shorter length cannula bodies permit increased angular degrees of freedom for instruments passing therethrough. Embodiments of shorter cannula bodies also accommodate curved instruments. The trocar comprises any suitable biocompatible material. In some embodiments, the trocar comprises a flexible material.

In embodiments in which the trocar and obturator are inserted through a gel pad, potential damage to underlying tissue by contact with the tip is reduced because the gel pad serves as an artificial body wall that is spaced from the underlying tissue as discussed above. The adaptable obturator is inserted into the trocar and together they are pushed through the gel pad with a penetration or insertion force of sufficient magnitude to result in penetration through the gel pad. In one embodiment, multiple sized trocars are provided for use with the access device, e.g., the gel pad, and thus a corresponding number of obturators sized to be used with such trocars are also provided. However, in accordance with various embodiments of the adaptable obturator, such an obturator replaces the numerous obturators previously provided for use with such access devices and thereby reducing or eliminating material, manufacturing, packaging and other similar expenses and operating confusion while maintaining or not varying the insertion force utilized or tactile feedback provided. Thus, a single adaptable obturator can be used with multiple various sized trocars. Accordingly, in various embodiments, it is the single adaptable obturator that conforms to the dimensions of the cannula and not the cannula conforming to the dimensions of the obturator and thereby providing a consistent or non-obstructive access pathway and internal and/or external cannula surfaces avoiding for example tissue trauma and/or instrument obstructions or potential damage.

Although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. As such, it should be appreciated that although specific combinations of embodiments and features or aspects of various embodiments may not be explicitly described such combinations however are contemplated and within the scope of the present inventions. Thus, it is intended that the scope of the present inventions herein disclosed should not be limited by the particular disclosed embodiments described above, but should be determined only by a fair reading of the claims.

The invention claimed is:

1. A trocar system comprising:
a first trocar having a seal assembly and a cannula with a diameter and a length;
a second trocar having a seal assembly and a cannula with a diameter larger than the diameter of the first trocar and a length greater than the length of the first trocar;
an adjustable obturator having a compressible portion in an initial state configured to have a diameter greater or equal to the diameter of the second trocar and in a compressed state configured to have a diameter greater or equal to the diameter of the first trocar and having a diameter smaller than the diameter of the second trocar.

2. The trocar system of claim 1 wherein the adjustable obturator having a handle, elongate shaft and a tip.

3. The trocar system of claim 1 wherein the adjustable obturator has a core seal.

4. The trocar system of claim 3 wherein the adjustable obturator has a depth limiter.

5. The trocar system of claim 1 further comprising a surgical access device with the adjustable obturator adapted to extend through the access device.

6. The trocar system of claim 5 wherein the surgical access device further comprises a gel material.

7. The trocar system of claim 6 further comprising a cap ring surrounding the gel material.

8. The trocar system of claim 7 further comprising a body wall liner adapted to be coupled to the cap ring.

9. The trocar system of claim 1 wherein the adjustable obturator has a first expanded portion positioned adjacent to the handle and adapted to abut against a cap of the first trocar.

10. The trocar system of claim 9 wherein the adjustable obturator has a second expanded portion positioned ahead of the first expanded portion, the second expanded portion adapted to abut against a cap of the second trocar and the first expanded portion adapted to pass through the cap of the second trocar.

11. The trocar system of claim 1 wherein the adjustable obturator further comprises a tip skirt adjacent to the compressible portion.

12. The trocar system of claim 1 wherein the adjustable obturator has a visual pathway extending through an elongate shaft of the adjustable obturator.

13. The trocar system of claim 1 wherein the tip is movable based on the state of the compressible portion.

14. The trocar system of claim 1 wherein the adjustable obturator has an insufflation pathway extending along the adjustable obturator.

15. The trocar system of claim 1 wherein the first trocar having a valve assembly having an instrument seal and the core seal having a sealing relationship with the instrument seal when the adjustable obturator is inserted fully therethrough.

16. The trocar system of claim 1 wherein the cannula of the first and second trocars are rigid and not compressible.

17. The trocar system of claim 1 wherein the compressible portion is not twistable or inflatable.

* * * * *